(12) United States Patent
Miyaji

(10) Patent No.: US 11,216,578 B2
(45) Date of Patent: Jan. 4, 2022

(54) DATA ANALYSIS METHOD AND DATA ANALYSIS SYSTEM

(71) Applicant: OSAKA UNIVERSITY, Osaka (JP)

(72) Inventor: Atsuko Miyaji, Osaka (JP)

(73) Assignee: OSAKA UNIVERSITY, Osaka (JP)

( * ) Notice: Subject to any disclaimer, the term of this patent is extended or adjusted under 35 U.S.C. 154(b) by 287 days.

(21) Appl. No.: 16/473,286

(22) PCT Filed: Dec. 26, 2017

(86) PCT No.: PCT/JP2017/046729
§ 371 (c)(1),
(2) Date: Jun. 25, 2019

(87) PCT Pub. No.: WO2018/124104
PCT Pub. Date: Jul. 5, 2018

(65) Prior Publication Data
US 2020/0004981 A1   Jan. 2, 2020

(30) Foreign Application Priority Data
Dec. 26, 2016 (JP) .............................. JP2016-252102

(51) Int. Cl.
*G06F 21/62* (2013.01)
*G16H 10/60* (2018.01)
(Continued)

(52) U.S. Cl.
CPC ........ *G06F 21/6227* (2013.01); *G06F 16/116* (2019.01); *G06F 16/9535* (2019.01); *G06Q 50/22* (2013.01); *G16H 10/60* (2018.01)

(58) Field of Classification Search
CPC .......... G06F 21/00; G06F 21/60; G06F 21/62; G06F 21/64; G06F 12/00; G06F 16/116;
(Continued)

(56) References Cited

U.S. PATENT DOCUMENTS 6,804,667 B1 * 10/2004 Martin .............. G06F 16/24556
707/754
7,181,017 B1 * 2/2007 Nagel .................. H04L 9/0825
380/282
(Continued)

FOREIGN PATENT DOCUMENTS

WO   2015/131394   9/2015

OTHER PUBLICATIONS

International Search Report (ISR) dated Mar. 27, 2018 in International (PCT) Application No. PCT/JP202017/046729.
(Continued)

*Primary Examiner* — Sheree N Brown
(74) *Attorney, Agent, or Firm* — Wenderoth, Lind & Ponack, L.L.P.

(57) ABSTRACT

According to a data analysis method by which time required for data analysis is shortened and practicality is improved, a client terminal requests institution terminals to perform analysis of a matching attribute; each of the institution terminals encrypts an element belonging to the matching attribute within a database and sends the converted data to an outsource terminal; the outsource terminal integrates the plurality of converted data sent from the institution terminals and sends the integrated converted data to the institution terminals; and each of the institution terminals compares each matching attribute of a plurality of the elements within the database of the institution terminal against the integrated converted data, thereby identifying, as a common element, an element associated with the matching attribute and held in common by the institution terminals.

8 Claims, 22 Drawing Sheets

(51) Int. Cl.
*G06F 16/9535* (2019.01)
*G06F 16/11* (2019.01)
*G06Q 50/22* (2018.01)

(58) Field of Classification Search
CPC .............. G06F 16/2458; G06F 16/2471; G06F 16/9535; G06F 21/6227; G06F 21/6254; G06F 21/6218; G06Q 50/22; G16H 10/60; G16H 10/00; G16H 50/70; H04L 2209/46; H04L 2209/805; H04L 2209/88; H04L 9/008
USPC ........................................................ 707/705
See application file for complete search history.

(56) References Cited

U.S. PATENT DOCUMENTS

| 7,668,820 | B2* | 2/2010 | Zuleba | G16H 10/60 707/765 |
|---|---|---|---|---|
| 2002/0010679 | A1* | 1/2002 | Felsher | G06Q 20/3674 705/51 |
| 2005/0102619 | A1* | 5/2005 | Hijikata | G06Q 10/10 715/254 |
| 2007/0100768 | A1* | 5/2007 | Boccon-Gibod | H04L 9/0825 705/59 |
| 2007/0185814 | A1* | 8/2007 | Boccon-Gibod | G06F 21/10 705/51 |
| 2007/0204078 | A1* | 8/2007 | Boccon-Gibod | G06F 21/64 710/54 |
| 2008/0046292 | A1* | 2/2008 | Myers | G06F 16/283 705/3 |
| 2010/0054477 | A1* | 3/2010 | Chew | H04L 9/0825 380/277 |
| 2010/0125903 | A1* | 5/2010 | Devarajan | G06F 21/577 726/15 |
| 2010/0241595 | A1* | 9/2010 | Felsher | G06Q 10/10 705/400 |
| 2011/0125527 | A1* | 5/2011 | Nair | G16H 50/70 705/3 |
| 2011/0125528 | A1* | 5/2011 | Padate | G16H 40/20 705/3 |
| 2014/0012862 | A1 | 1/2014 | Kawamoto et al. | |

OTHER PUBLICATIONS

Lea Kissner, et al., "Privacy-Preserving Set Operations", Crypto 2005, LNCS vol. 3621, pp. 241-257, Aug. 2005.
Dilip Many, et al., "Fast Private Set Operations with SEPIA", Technical Report, 345, pp. 1-11, Mar. 2012.
Extended European Search Report dated Oct. 24, 2019 in corresponding European Patent Application No. 17889263.4.

* cited by examiner

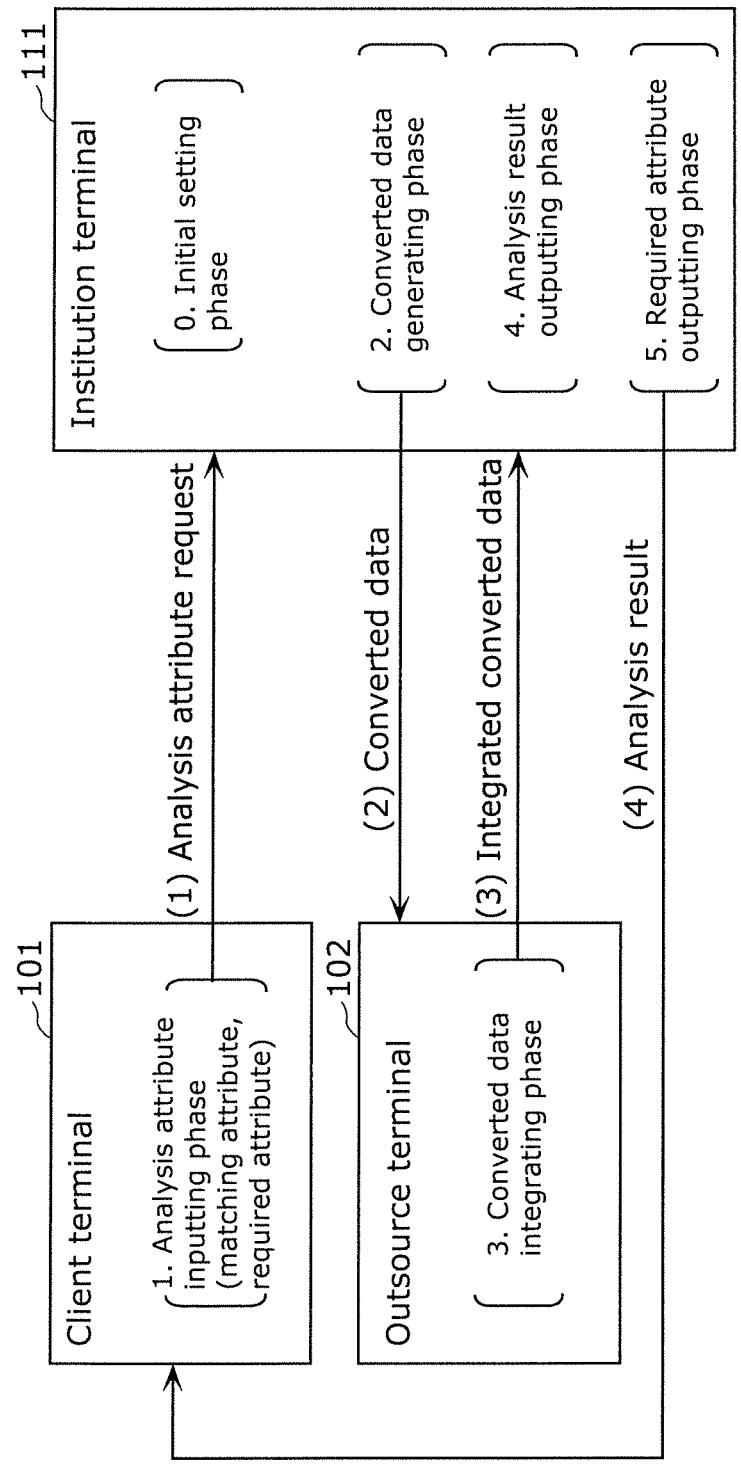

FIG. 3

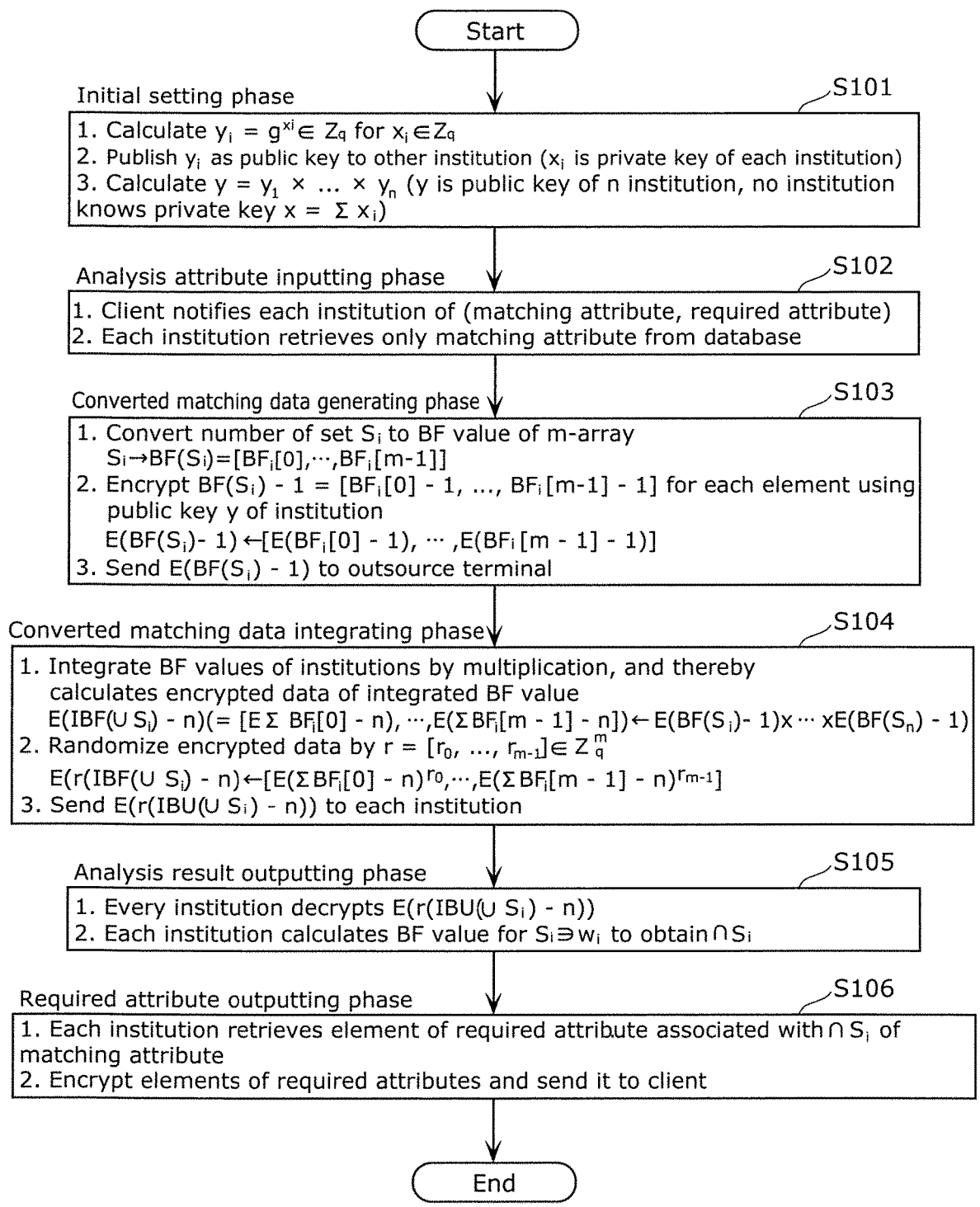

```
                              ┌───────┐
                              │ Start │
                              └───┬───┘
Initial setting phase             ▼                            S101
┌─────────────────────────────────────────────────────────────────┐
│ 1. Calculate $y_i = g^{x_i} \in Z_q$ for $x_i \in Z_q$          │
│ 2. Publish $y_i$ as public key to other institution ($x_i$ is private key of each institution) │
│ 3. Calculate $y = y_1 \times \ldots \times y_n$ ($y$ is public key of n institution, no institution │
│ knows private key $x = \Sigma x_i$)                             │
└─────────────────────────────────────────────────────────────────┘

Analysis attribute inputting phase                              S102
┌─────────────────────────────────────────────────────────────────┐
│ 1. Client notifies each institution of (matching attribute, required attribute) │
│ 2. Each institution retrieves only matching attribute from database │
└─────────────────────────────────────────────────────────────────┘

Converted matching data generating phase                        S103
┌─────────────────────────────────────────────────────────────────┐
│ 1. Convert number of set $S_i$ to BF value of m-array           │
│    $S_i \to BF(S_i) = [BF_i[0], \ldots, BF_i[m-1]]$             │
│ 2. Encrypt $BF(S_i) - 1 = [BF_i[0] - 1, \ldots, BF_i[m-1] - 1]$ for each element using │
│    public key y of institution                                  │
│    $E(BF(S_i) - 1) \leftarrow [E(BF_i[0] - 1), \ldots, E(BF_i[m-1] - 1)]$ │
│ 3. Send $E(BF(S_i) - 1)$ to outsource terminal                  │
└─────────────────────────────────────────────────────────────────┘

Converted matching data integrating phase                       S104
┌─────────────────────────────────────────────────────────────────┐
│ 1. Integrate BF values of institutions by multiplication, and thereby │
│    calculates encrypted data of integrated BF value             │
│    $E(IBF(\cup S_i) - n)(= [E\Sigma BF_i[0] - n), \ldots, E(\Sigma BF_i[m-1] - n)]) \leftarrow E(BF(S_i) - 1) \times \ldots \times E(BF(S_n) - 1)$ │
│ 2. Randomize encrypted data by $r = [r_0, \ldots, r_{m-1}] \in Z_q^m$ │
│    $E(r(IBF(\cup S_i) - n) \leftarrow [E(\Sigma BF_i[0] - n)^{r_0}, \ldots, E(\Sigma BF_i[m-1] - n)^{r_{m-1}}]$ │
│ 3. Send $E(r(IBU(\cup S_i) - n))$ to each institution           │
└─────────────────────────────────────────────────────────────────┘

Analysis result outputting phase                                S105
┌─────────────────────────────────────────────────────────────────┐
│ 1. Every institution decrypts $E(r(IBU(\cup S_i) - n))$         │
│ 2. Each institution calculates BF value for $S_i \ni w_i$ to obtain $\cap S_i$ │
└─────────────────────────────────────────────────────────────────┘

Required attribute outputting phase                             S106
┌─────────────────────────────────────────────────────────────────┐
│ 1. Each institution retrieves element of required attribute associated with $\cap S_i$ of │
│    matching attribute                                           │
│ 2. Encrypt elements of required attributes and send it to client │
└─────────────────────────────────────────────────────────────────┘

┌───────┐
                              │  End  │
                              └───────┘
```

DATA ANALYSIS METHOD AND DATA ANALYSIS SYSTEM

TECHNICAL FIELD

The present invention relates to a method and a system for analyzing data.

BACKGROUND ART

In these years, with the spread of IoT (Internet of Things), data transmitted from transmission sources including humans and objects are collected as big data, and not only the amount of data but also the number of institutions that collect data are rapidly increasing.

In view of this, a data analysis method that identifies the intersection, union, or size of data provided from a plurality of institutions has been proposed (for example, see Non Patent Literature (NPL) 1 or 2).

Typically, data is collected and stored independently by each institution such as a hospital. In the above proposed data analysis method, data stored in each of institutions is treated as a set of a plurality of elements belonging to one attribute, and whether or not the institutions have the same element is determined.

CITATION LIST

Non Patent Literature

[NPL 1] L. Kissner and D. Song. Privacy-preserving set operations. In CRYPTO 2005, volume 3621 of LNCS, pages 241-257. Springer, 2005

[NPL 2] D. Many, M. Burkhart, and X. Dimitropoulos. Fast private set operations with sepia. Technical Report, 345, 2012

SUMMARY OF INVENTION

Technical Problem

However, the data analysis method disclosed in the above described NPL 1 has a problem that as the number of institutions increases, it takes a more significant amount of time. Further, the data analysis method disclosed in the above described NPL 2 has a problem that it needs a reliable institution which keeps institutions' data secret, in other words, an institution capable of obtaining other institutions' data (i.e., a data depository facility), and therefore is difficult to practice.

In view of these problems, the present invention provides a data analysis method by which a time required for data analysis is shortened, a reliable institution is unnecessary, and practicality is improved.

Solution to Problem

In order to achieve the aforementioned object, a data analysis method according to the present invention includes: by a client terminal, requesting a plurality of institution terminals to perform analysis of a matching attribute, each of the institution terminals holding a database that indicates a plurality of elements with respect to each of one or more attributes; by each of the plurality of institution terminals, in response to the request from the client terminal, performing conversion processing including encryption on an element belonging to the matching attribute within the database of the institution terminal, and sending converted data obtained by the conversion processing to an outsource terminal; by the outsource terminal, integrating a plurality of the converted data sent from the plurality of institution terminals to generate integrated converted data, and sending the integrated converted data to each of the plurality of institution terminals; by each of the plurality of institution terminals, comparing each of a plurality of the elements belonging to the matching attribute within the database of the institution terminal with the integrated converted data sent from the outsource terminal, to identify, as a common element, an element belonging to the matching attribute and held in common by at least two of the plurality of institution terminals. It is noted that each of the plurality of institution terminals has a database of, for example, medical examination results obtained by the institution such as a hospital or a school.

In this way, the outsource terminal integrates converted data sent from each of the plurality of institution terminals, and the integrated converted data composed of the plurality of converted data is sent to each of the plurality of institution terminals. Therefore, the plurality of institution terminals bear not all of the computation required for analysis of the matching attribute, and a part of the computation for the institution terminals can be aggregated on the outsource terminal. As a result, even if the number of institution terminals subjected to analysis, that is, the number of institutions increases, the overall amount of computation required for data analysis can be restrained, and the time required for data analysis, that is, comparison of a matching attribute can be shortened. In other words, while conventionally, the load of data analysis depends on the number of institutions, such dependency can be restrained. In addition, data can be restrained from being collected by one institution, and it is possible to request the outsource terminal to perform computation which depends on the number of institutions.

In addition, since converted data sent from each of the plurality of institution terminals to the outsource terminal has been encrypted, the outsource terminal cannot decrypt the converted data to the elements even if acquiring the converted data. However, even though the converted data cannot be decrypted, the integrated converted data necessary for identifying a common element is generated by the outsource terminal. Therefore, according to a data analysis method of the present invention, the outsource terminal does not need to be a terminal device of a reliable institution which keeps data secret, and the practicality can be improved.

In addition, the integrated converted data sent from the outsource terminal to each of the plurality of institution terminals is data into which a plurality of converted data are integrated. Therefore, even if each of the plurality of institution terminals acquires the integrated converted data from the outsource terminal and further decrypts it, each of the plurality of institution terminals cannot know elements held by the other institution terminals except for the common element. Accordingly, the content of the database held by each of the plurality of institution terminals can be kept secret from the other institution terminals as well as the outsource terminal. As a result, for example, privacy can be protected.

Furthermore, the client terminal may be one of the plurality of institution terminals and requests a plurality of remaining institution terminals to perform analysis of the matching attribute, the plurality of remaining institution terminals being the plurality of institution terminals excluding the client terminal. Furthermore, the outsource terminal may be one of the plurality of institution terminals and sends the integrated converted data to a plurality of remaining institution terminals, the plurality of remaining institution terminals being the plurality of institution terminals excluding the outsource terminal.

Furthermore, when performing the conversion processing on the element belonging to the matching attribute, each of the plurality of institution terminals may apply a Bloom filter to the element to convert the element to a BF value including at least one integer, and encrypts the BF value.

Accordingly, since the elements are converted to BF values independent from their data size, the load of comparing each of the plurality of elements belonging to the matching attribute within the database with the integrated converted data can be reduced, so that processing speed can be improved.

Furthermore, the client terminal may further request each of the plurality of institution terminals to perform analysis of a required attribute, and each of the plurality of institution terminals may further select, as an output element, an element associated with the common element from a plurality of elements belonging to the required attribute indicated by the database held by the institution terminal, and send, as an analysis result, the common element and the output element to the client terminal.

In conventional data analysis methods, data stored in each institution is treated as a set of a plurality of elements with one attribute. However, data has a plurality of attributes in general, and the conventional data analysis methods cannot handle such data having a plurality of attributes, and are not stable for practical use.

In view of this, according to the present invention, analysis is performed by using a matching attribute and a required attribute as described above. Thereby, typical data having a plurality of attributes (i.e., database) can be handled, and the practicality can be further improved.

Furthermore, the client terminal may further acquire a plurality of the analysis results sent respectively from the plurality of institution terminals, and integrate the output elements contained respectively in the plurality of analysis results.

Thereby, the output elements sent from each of the plurality of institution terminals are acquired by the client terminal, and the output elements from the plurality of institution terminals are integrated by the client terminal. Thereby, integration of any databases can be securely realized while privacy is protected, dependency on the number of institutions is prevented, and the number of attributes of the databases is not restricted.

Furthermore, in requesting the analysis of the required attribute, the client terminal may impose a condition for obtaining the analysis result on each of the plurality of institution terminals. For example, in requesting the analysis of the required attribute, the client terminal imposes, as the condition, a condition that the required attribute is contained in at least two of the plurality of institution terminals.

Note that these generic or specific aspects may be implemented as a system, a method, an integrated circuit, a computer program, or a computer-readable recording medium such as a CD-ROM, or may be implemented as any combination of a system, a method, an integrated circuit, a computer program, and a recording medium.

Advantageous Effects of Invention

According to a data analysis method of the present invention, time required for data analysis can be shortened, and practicality can be improved.

BRIEF DESCRIPTION OF DRAWINGS

FIG. 2 is a diagram illustrating processes of a client terminal, an outsource terminal, and an institution terminal in the data analysis system of the embodiment.
FIG. 3 is a flowchart of a processing operation of the data analysis system of the embodiment.

DESCRIPTION OF EMBODIMENTS

Hereinafter, embodiments will be described in detail with reference to the drawings.

Note that the embodiments described below each show a generic or specific example. The numerical values, shapes, materials, structural components, the arrangement and connection of the structural components, steps, the processing order of the steps, etc. shown in the following embodiments are mere examples, and thus are not intended to limit the present invention. Of the structural components described in the following embodiments, structural components not recited in any one of the independent claims that indicate the broadest concepts will be described as optional structural components. Furthermore, the respective figures are schematic diagrams and are not necessarily precise illustrations. Moreover, in the figures, the same structural component is given the same reference sign.

Embodiment 1

Figure 1:
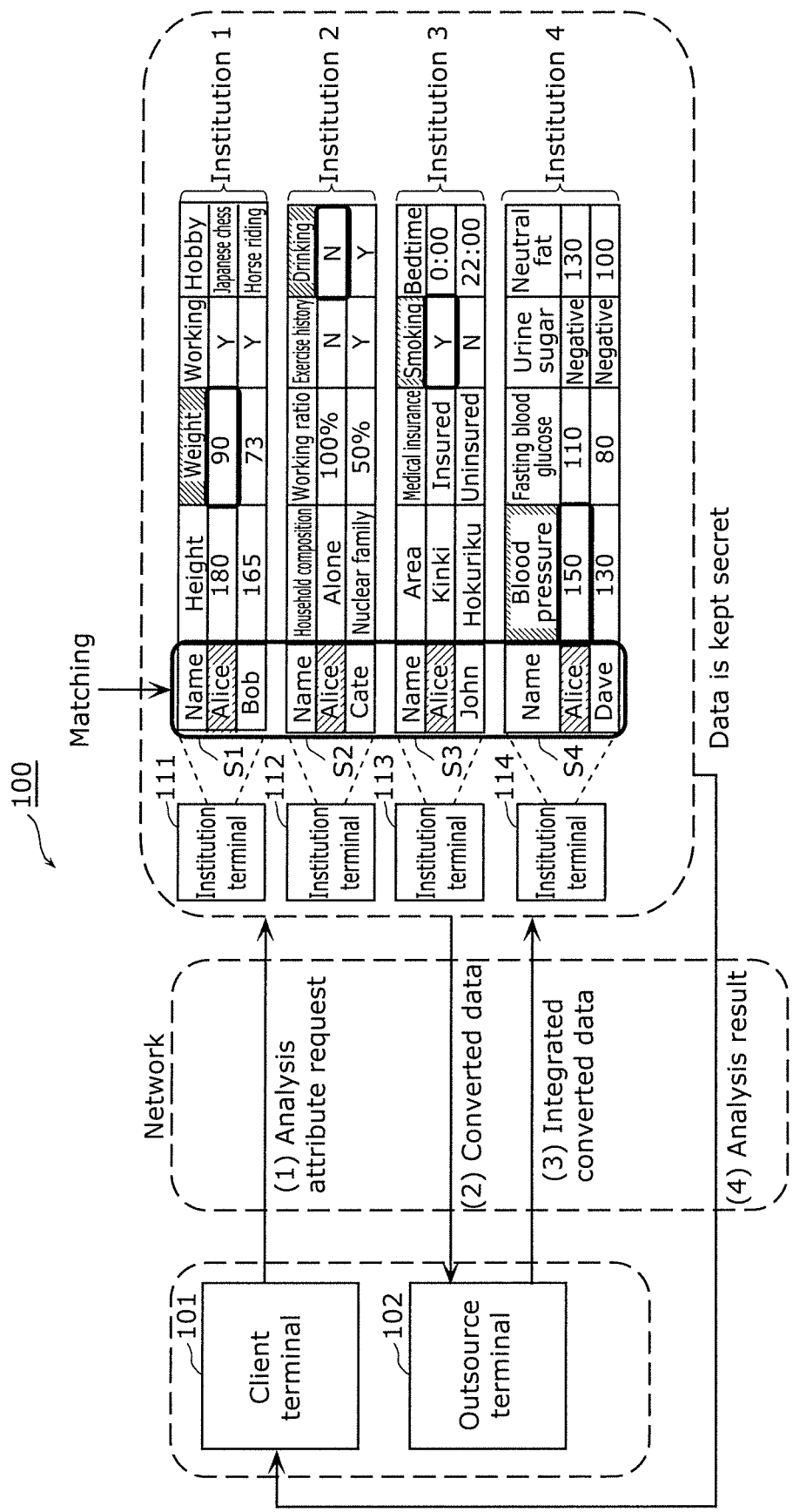
FIG. 1 is a configuration diagram of a data analysis system according to an embodiment.

FIG. 1 is a configuration diagram of a data analysis system according to the present embodiment.

A data analysis system 100 according to the present embodiment includes a client terminal 101, an outsource terminal 102, and institution terminals 111-114, which are connected by a network such as the Internet.

The client terminal 101 is a terminal device manipulated by a client who requests data analysis.

Each of the institution terminals 111-114 is a terminal device installed in a data holding institution such as a hospital, a company, or a school (hereinafter simply referred to as an institution), and holds a database generated or acquired in that institution. Specifically, the institution terminal 111 holds a database S1, the institution terminal 112 holds a database S2, the institution terminal 113 holds a database S3, and the institution terminal 114 holds a database S4.

The databases S1 to S4 indicate a plurality of attributes, and a plurality of elements belonging to each of the plurality of attributes. For example, one of the plurality of attributes is name, height, weight, working/nonworking, hobby, household composition, working ratio, exercise history, drinking, area, medical insurance, smoking, bedtime, blood pressure, fasting blood glucose, urine sugar, or neutral fat. An element may be a numerical value (hereafter also referred to as attribute value), a character, a character string, or a flag indicating presence or absence.

The outsource terminal 102 is a terminal device that acquires data from each of the institution terminals 111-114 and processes it.

In the above described data analysis system 100, at first, the client terminal 101 sends an analysis attribute request to the institution terminals 111-114. The analysis attribute request indicates a matching attribute and a required attribute. The matching attribute is, for example, "name".

Upon receiving such an analysis attribute request, each institution's institution terminal 111-114 selects the matching attribute (e.g., "name") indicated by the analysis attribute request from a plurality of attributes indicated in the database held by oneself. Then, each of the institution terminals 111-114 generates a converted data as described later using elements belonging to the matching attribute, and sends the converted data to the outsource terminal 102. Specifically, the institution terminal 111 generates converted data using an element "Alice" belonging to the attribute "name".

The outsource terminal 102 acquires converted data from each institution's institution terminal 111-114, and generates integrated converted data from their converted data. Then, the outsource terminal 102 sends the generated integrated converted data to each of the institution terminals 111-114.

Upon acquiring the integrated converted data from the outsource terminal 102, each of the institution terminals 111-114 compares each of elements belonging to the matching attribute within the database held by oneself with the integrated converted data. By this comparing, each of the institution terminals 111-114 finds out, as a common element, an element belonging to the respective matching attributes of the databases S1 to S4 in common. For example, each of the institution terminals 111-114 finds out, as a common element, the element "Alice" which belongs to the respective matching attributes "name" of the databases S1 to S4 in common.

Then, each of the institution terminals 111-114 selects the required attribute indicated by the above described analysis attribute request from the plurality of attributes indicated in the database held by oneself. Specifically, the institution terminal 111 selects an attribute "weight" as a required attribute. The institution terminal 112 selects an attribute "drinking" as a required attribute. The institution terminal 113 selects an attribute "smoking" as a required attribute. The institution terminal 114 selects an attribute "blood pressure" as a required attribute.

Then, each of the institution terminals 111-114 selects, as an output element, an element associated with the common element belonging to the above described matching attribute from a plurality of elements belonging to the required attribute of the database held by oneself. Then, each of the institution terminals 111-114 sends, as an analysis result, these common element and output element to the client terminal 101.

FIG. 2 is a diagram illustrating processes of the client terminal 101, the outsource terminal 102, and the institution terminal 111 in the data analysis system 100. Although the process of the institution terminal 111 is illustrated in FIG. 2, each of the institution terminals 112-114 also performs processing as in the institution terminal 111.

In the data analysis system 100 in the present embodiment, processing is performed in six phases: 0th to fifth phases.

The 0th phase is an initial setting phase in which the institution terminal 111 performs initial setting for performing cryptographic communication with the client terminal 101 and the outsource terminal 102.

The first phase is an analysis attribute inputting phase. In this phase, the client terminal 101 acquires a matching attribute and a required attribute based on, for example, operation by a client. Then, the client terminal 101 sends an analysis attribute request indicating the matching attribute and the required attribute to each of the institution terminals 111-114.

The second phase is a converted data generating phase. In this phase, the institution terminal 111 generates converted data as described above and sends it to the outsource terminal 102.

The third phase is a converted data integrating phase. In this phase, the outsource terminal 102 integrates the converted data acquired from each of the institution terminals 111-114 to generate integrated converted data. Further, in this phase, the outsource terminal 102 sends the generated integrated converted data to each of the institution terminals 111-114.

The fourth phase is an analysis result outputting phase. In this phase, the institution terminal 111 compares the database S1 held by oneself using the integrated converted data, thereby outputting inside the institution terminal 111, as a part of analysis result, a common element as described above.

The fifth phase is a required attribute outputting phase. In this phase, the institution terminal 111 selects, as an output element, an element associated with the common element from a plurality of elements belonging to the required attribute within the database S1 held by oneself, and sends, as the analysis result, the common element and the output element to the client terminal 101.

FIG. 3 is a flowchart of a processing operation of the data analysis system 100. In this flowchart of FIG. 3, i is an identifier for identifying any one of n (n is an integer more than one) institutions (or institution terminals). In the examples of FIG. 1 or FIG. 2, any one of the four institutions 1-4 (or institution terminals 111-114) is identified by i.

First, in the initial setting phase (step S101), an institution terminal i calculates $y_i=g^{xi} \in Z_q$ for $x_i \in Z_q$. $y_i$ is published as a public key of the institution terminal i to each of other institution terminals than the institution terminal i. $x_i$ is a private key of the institution terminal i. Then, the institution terminal i calculates $y=y_1 \times \ldots \times y_n$. y is a public key of n institution terminals. It is noted that no institution terminal knows a private key $x=\Sigma xi$.

Then, in the analysis attribute inputting phase (step S102), the client terminal 101 sends an analysis attribute request to each institution terminal to notify each institution terminal of a matching attribute and a required attribute. Further, in this analysis attribute inputting phase, upon receiving the matching attribute and required attribute from the client terminal 101, each the institution terminal retrieves a plurality of elements belonging only to the notified matching attribute from the database hold by oneself. It is noted that a set composed of a plurality of elements belonging to a matching attribute in the institution terminal i's database is represented as $Si=\{v_1, \ldots, v_{wi}\}$. Each of $v_1, \ldots, v_{wi}$ is an element of the set, and wi, which is the number of data (the number of elements), is represented as wi=|Si|.

Then, in the converted data generating phase (step S103), the institution terminal i generates converted data. Specifically, the institution terminal i applies a Bloom filter to every matching attribute of each element of set $Si=\{v_{wi}, \ldots, v_{wi}\}$ to convert the attribute value to a BF value. BF value is an array of data composed of m (m is an integer greater than or equal to 1) binary values (0 or 1). In other words, the institution terminal i converts the matching attribute of each element of set Si to $BF(Si)=[BFi(0), \ldots, BFi(m-1)]$. Each of $BFi(0), \ldots, BFi(m-1)$ is an element of the array, and is a binary value of 0 or 1. Although BF value is assumed to be an array composed of m binary values in the present embodiment, multivalued values may be used instead of binary values. Therefore, BF value may be an array composed of m integer values.

Then, the institution terminal i obtains an array of $BF(Si)-1=[BFi[0]-1, \ldots, BFi[m-1]-1]$ by subtracting 1 from each element of the above described array. It is noted that this array is composed of m elements, each of which is 0 or -1. Further, the institution terminal i encrypts the array of $BF(Si)-1=[BFi[0]-1, \ldots, BFi[m-1]-1]$ for each of the elements contained in the array, using the public key y of the n institution terminals. For this encryption, homomorphic encryption, for example, exponential ElGamal encryption is used. In the exponential ElGamal encryption, the power of m, that is, $g^m$ is encrypted instead of m. By this encryption, the institution terminal i generates $[E(BFi[0]-1), \ldots, E(BFi[m-1]-1)]$, that is, $E(BF(Si)-1)$. Then, the institution terminal i sends the $E(BF(Si)-1)$ to the outsource terminal 102 as the converted data. Then, in the converted data integrating phase (step S104), upon acquiring the converted data $E(BF(Si)-1)$ from each of the n institution terminals, the outsource terminal 102 integrates these $E(BF(Si)-1)$. Specifically, the outsource terminal 102 multiplies the n number of $E(BF(Si)-1)$. As a result from $E(BF(S1)-1) \times \ldots \times E(BF(Sn)-1)$, the outsource terminal 102 calculates encrypted data of the integrated BF value $E(IBU(\cup Si)-n)=[E(EBFi[0]-n), E(EBFi[m-1]-n)]$. Further, the outsource terminal 102 randomizes the encrypted data by $r=[r_0, \ldots, r_{m-1}] \in Z_q^m$. As a result, the outsource terminal 102 calculates $[E(\Sigma BFi[0]-n)^{r_0}, \ldots, E(\Sigma BFi[m-1]-n)^{r_{m-1}}]$ as $E(r(IBU(\cup Si)-n))$. Then, the outsource terminal 102 sends $E(r(IBU(\cup Si)-n))$ to the n institution terminals as integrated converted data.

Then, in the analysis result outputting phase (step S105), upon acquiring the integrated converted data $E(r(IBU(\cup Si)-n))$ from the outsource terminal 102, the institution terminal i decrypts the $E(r(IBU(\cup Si)-n))$. Specifically, each of all the institution terminal i decrypts $E(r(IBU(\cup Si)-n))$ in collaboration with all of the institution terminals i using the private key xi of the institution terminal i, which is its own private key, thereby acquiring $r(IBU(\cup Si)-n)=[(\Sigma BFi[0]-n)^{r_0}, \ldots, (\Sigma BFi[m-1]-n)^{r_{m-1}}]$. Then, the institution terminal i compares the result of application of the Bloom filter to the matching attribute of each of wi elements of the set Si with the acquired array $r(IBU(\cup Si)-n)=[(\Sigma BFi[0]-n)^{r_0}, \ldots, (\Sigma BFi[m-1]-n)^{r_{m-1}}]$, thereby determining whether or not the element associated with the matching attribute of each element of the set Si of the matching attribute is a common element ($\cap Si$) which is common in the n institution terminals.

As described above, BF(Si) of each matching attribute of each element of the set Si is an array composed of m elements, each of which is 0 or 1. In addition, $r(IBU(\cup Si)-n)=[(\Sigma BFi[0]-n)^{r_0}, (\Sigma BFi[m-1]-n)^{r_{m-1}}]$ is an array composed of m values including 0 as a value. In a case where converted data corresponding to an element common in n institution terminals is sent from the n institution terminals to the outsource terminal 102, a value contained in BF(Si) of the common element is contained as a value of 0 in r(IBU ($\cup Si$)-n). Therefore, a value of 0 contained in (BF(Si)-1) of the common element exists as a value of 0 even after integration, randomization, and the like of the converted data. For example, if BF(Si) of an element associated with the matching attribute which is common in n institution terminals is an array (1, 0, 1, 1, ... 0, 1), $r(IBU(\cup Si)-n)$ will be an array (0, a, 0, 0, ... b, 0) (where a and b are arbitrary values). Therefore, the institution terminal i finds out, as a common element, an element of Si corresponding to BF(Si) in which a value of 1 is placed in the same position as a value of 0 of $r(IBU(\cup Si)-n)$, from among BF(Si) of a plurality of elements contained in the set Si held by oneself.

It is noted that processing of each of the above described converted data generating phase, converted data integrating phase, and analysis result outputting phase is performed on each element of set Si. Accordingly, in these phases, sequential processing is performed on each element of the set $Si=\{v1, \ldots, vwi\}$ held by each of the n institution terminals, and its result is sent.

Then, in the required attribute outputting phase (step S106), the institution terminal i retrieves values of the required attributes associated with the common element ($\cap Si$) from a plurality of elements within the database held by oneself, as an output element from the database. Then, the institution terminal i encrypts the common element and output element, and sends the encrypted common element and output element to the client terminal 101 as analysis result.

In the present embodiment, since the outsource terminal 102 generates integrated converted data as described above, time required for data analysis can be shortened. In addition, since converted data sent from each of the n institution terminals to the outsource terminal 102 has been encrypted, the outsource terminal 102 cannot decrypt the converted data into the element even if acquiring the converted data. However, even though the converted data cannot be decrypted, the integrated converted data necessary for identifying a common element is generated by the outsource terminal 102. Therefore, according to a data analysis method of the present embodiment, the outsource terminal 102 does not need to be a terminal device of a reliable institution which keeps data secret, and the practicality can be improved.

Further, in the present embodiment, the integrated converted data sent from the outsource terminal 102 to each of the n institution terminals is data into which a plurality of converted data are integrated. Therefore, even if each of the n institution terminals acquires the integrated converted data from the outsource terminal 102 and further decrypts it, each of the n institution terminals cannot know elements held by the other institution terminals except for the common element. Accordingly, the content of the database held by each of the n institution terminals can be kept secret from the other institution terminals as well as the outsource terminal 102. As a result, for example, privacy can be protected.

Figure 4:
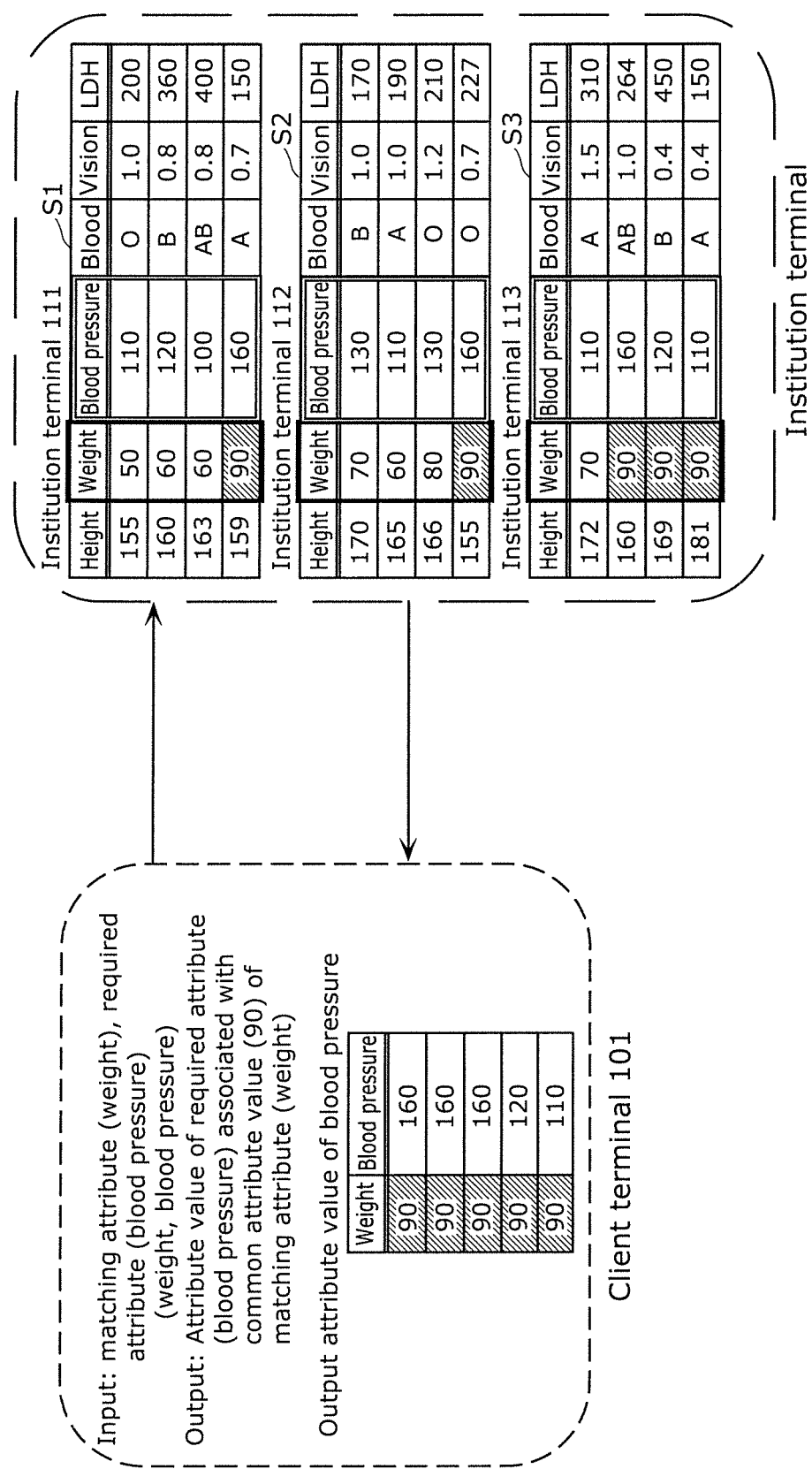
FIG. 4 is a diagram illustrating one example of analysis by the data analysis system of the embodiment.

FIG. 4 is a diagram illustrating one example of analysis by the data analysis system 100.

For example, the client terminal 101 deals with (weight, blood pressure) as (matching attribute, required attribute) based on operation by a client. Then, the client terminal 101 sends an analysis attribute request indicating the (weight, blood pressure) to the institution terminals 111-113. The institution terminals 111-113 perform processing of each of the above described initial setting phase, converted data generating phase, analysis result outputting phase, and required attribute outputting phase. As a result, the institution terminal 111 encrypts (weight, blood pressure)=(90, 160) contained in the database S1, which is medical examination data held by oneself, and sends them to the client terminal 101 as analysis result. The institution terminal 112 encrypts (weight, blood pressure)=(90, 160) contained in the database S2, which is medical examination data held by oneself, and sends them to the client terminal 101 as analysis result. The institution terminal 113 encrypts (weight, blood pressure)=(90, 160), (90, 120), and (90, 110) contained in the database S3, which is medical examination data held by oneself, and sends them to the client terminal 101 as analysis result.

The client terminal 101 acquires the analysis results sent from the institution terminals 111-113. Accordingly, from the databases S1 to S3 of the institution terminals 111-113, the client terminal 101 acquires an attribute value of blood pressure (an output element) associated with "90" which is a common attribute value (a common element) belonging to weight in the respective databases S1 to S3. Then, the client terminal 101 outputs or displays the weight "90", and body pressure's attribute values "160", "160", "160", "120", and "110" associated with the weight "90".

As described above, in the data analysis system 100 of the present embodiment, a client operating the client terminal 101 can obtain a required attribute value which is associated with a matching attribute and to be collected, while keeping medical examination data of each institution (institution terminal) secret.

Figure 5:
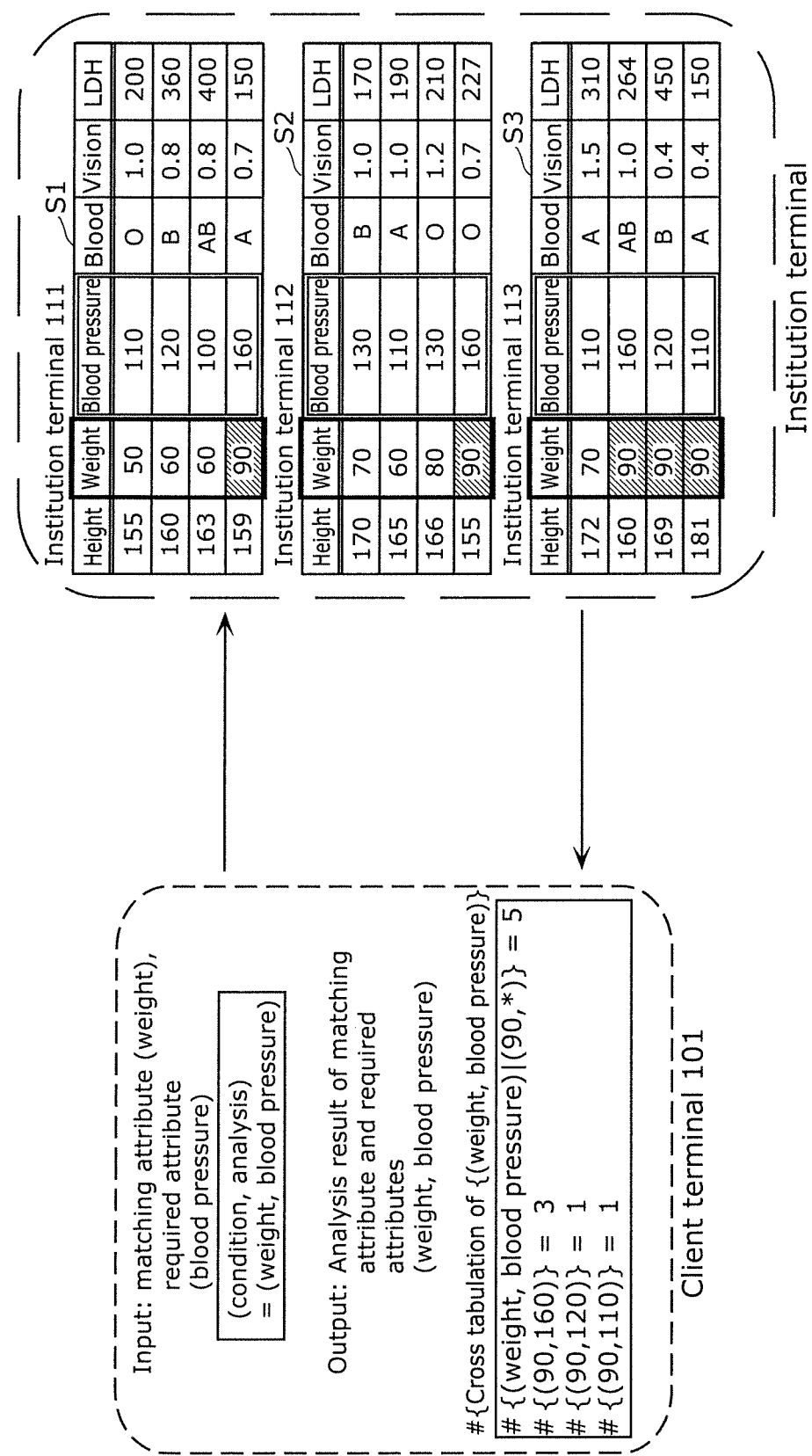
FIG. 5 is a diagram illustrating another example of analysis by the data analysis system of the embodiment.

FIG. 5 is a diagram illustrating another example of analysis by the data analysis system 100.

As in the example shown in FIG. 4, the client terminal 101 deals with (weight, blood pressure) as (matching attribute, required attribute) based on operation by a client. This matching attribute is an attribute which is a condition of analysis, and the required attribute is an attribute which is a target of analysis.

Then, the client terminal 101 sends an analysis attribute request indicating the (weight, blood pressure) to the institution terminals 111-113 as in the example shown if FIG. 4.

The institution terminal 111 encrypts (weight, blood pressure)=(90, 160) contained in the database S1 held by oneself, and sends them to the client terminal 101 as analysis result. The institution terminal 112 encrypts (weight, blood pressure)=(90, 160) contained in the database S2 held by oneself, and sends them to the client terminal 101 as analysis result. The institution terminal 113 encrypts (weight, blood pressure)=(90, 160), (90, 120), and (90, 110) contained in the database S3 held by oneself, and sends them to the client terminal 101 as analysis result.

The client terminal 101 acquires the analysis results sent from the institution terminals 111-113. Accordingly, from the databases S1 to S3 of the institution terminals 111-113, the client terminal 101 acquires an attribute value of blood pressure (an output element) associated with "90" which is a common attribute value (a common element) belonging to weight in the respective databases S1 to S3. Then, the client terminal 101 outputs or displays an aggregate result of blood pressure's attribute values associated with the weight "90". For example, the client terminal 101 displays that in the institutions of the institution terminals 111-113, there are five persons having weight "90" and there are three persons having weight "90" and blood pressure "160".

As described above, in the data analysis system 100 of the present embodiment, a client operating the client terminal 101 can obtain statistics associated with a matching attribute while keeping medical examination data of each institution (institution terminal) secret.

Figure 6:
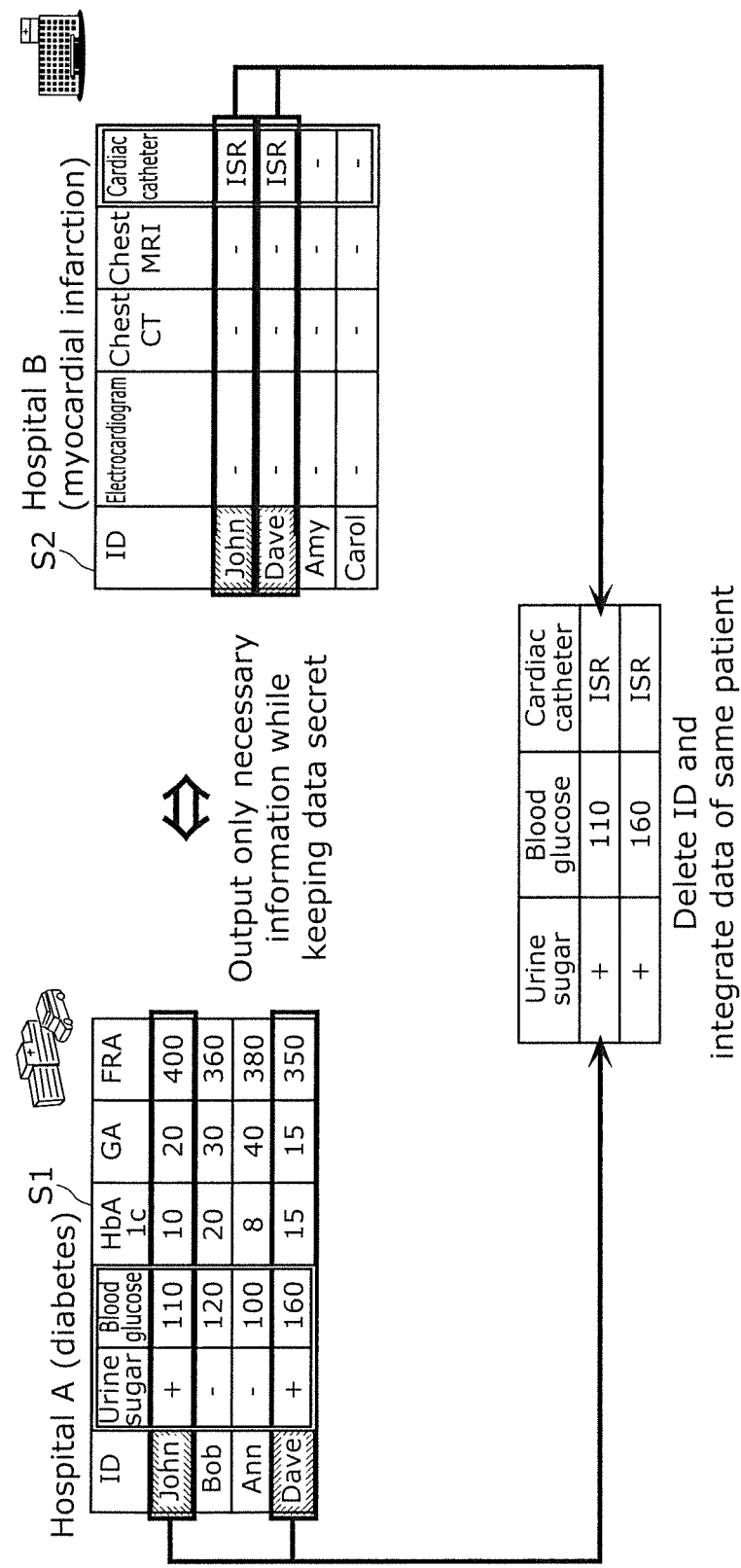
FIG. 6 is a diagram illustrating a further example of analysis by the data analysis system of the embodiment.

FIG. 6 is a diagram illustrating a further example of analysis by the data analysis system 100.

For example, the institution terminal 111 holds information acquired in a hospital A which is an institution that performs medical treatment of diabetes, as the database S1. ID, urine sugar, blood glucose, HbA1c, and so on in the database S1 are attributes of diabetic patients. This database S1 indicates a plurality of elements belonging to these attributes. The institution terminal 112 holds information acquired in a hospital B which is an institution that performs medical treatment of myocardial infarction, as the database S2. ID, electrocardiogram, chest CT, chest MRI, and so on in the database S2 are attributes of myocardial infarction patients. In this database S2, each of a plurality of elements includes the plurality of attributes.

In this case, the client terminal 101 deals with (ID, (urine sugar, blood glucose)) for the hospital A as (matching attribute, required attribute) and deals with (ID, cardiac catheter) for the hospital B as (matching attribute, required attribute), for example, based on operation by a client. Then, the client terminal 101 sends an analysis attribute request of a matching attribute (ID), and required attributes (urine sugar, blood glucose) to the institution terminal 111 of the hospital A, and sends an analysis attribute request of matching attribute (ID), and required attribute (cardiac catheter) to the institution terminal 112 of the hospital B.

The institution terminals 111 and 112 perform processing of each of the above described initial setting phase, converted data generating phase, analysis result outputting phase, and required attribute outputting phase. As a result, the institution terminal 111 encrypts (ID), (urine sugar), (blood glucose)=(John), (+), (110) and (Dave), (+), (160) contained in the database S1 held by oneself, and sends them to the client terminal 101 as analysis result. The institution terminal 112 encrypts (ID), (cardiac catheter)=(John), (ISR) and (Dave), (ISR) contained in the database S2 held by oneself, and sends them to the client terminal 101 as analysis result.

The client terminal 101 acquires the analysis results sent from the institution terminals 111 and 112. Accordingly, from the databases S1 and S2, the client terminal 101 acquires, as output elements, elements of urine sugar, blood glucose, and cardiac catheter associated with "John" which is a common element belonging to ID in the respective databases S1 and S2. Further, from the databases S1 and S2, the client terminal 101 acquires, as output elements, elements of urine sugar, blood glucose, and cardiac catheter associated with "Dave" which is a common element belonging to ID in the respective databases S1 and S2. Then, the client terminal 101 integrates the output elements of urine sugar, blood glucose, and cardiac catheter associated with ID "John", and integrates the output elements of urine sugar, blood glucose, and cardiac catheter associated with ID "Dave". During this integration, the client terminal 101 deletes ID "John" and ID "Dave". Thereby, data secrecy can be further improved.

In the above described example, the institution terminal 111 encrypts and sends (ID)=(John), (Dave), and (urine sugar, blood glucose)=(+, 110), (+, 160), and the institution terminal 112 encrypts and sends (ID)=(John), (Dave), and (cardiac catheter)=(ISR), (ISR). However, without sending an encrypted element belonging to ID (for example, "John" or "Dave"), the institution terminals 111 and 112 may convert the element belonging to the ID to a matching indicator, and encrypt and send the matching indicator.

Figure 7:
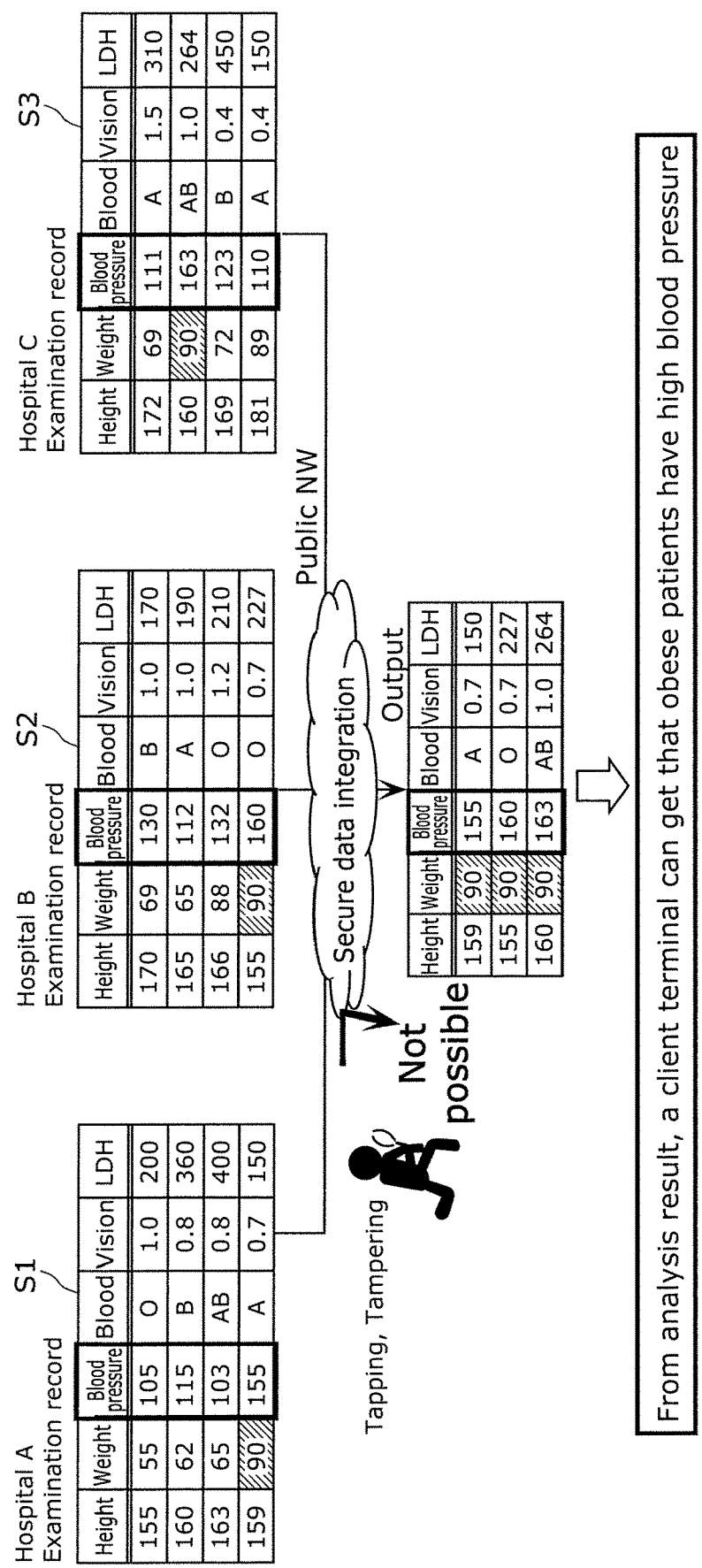
FIG. 7 is a diagram illustrating a further example of analysis by the data analysis system of the embodiment.

FIG. 7 is a diagram illustrating a further example of analysis by the data analysis system 100.

For example, the institution terminal 111 holds information recorded by examination in a hospital A which is an institution, as the database S1. The institution terminal 112 holds information recorded by examination in a hospital B which is an institution, as the database S2. The institution terminal 113 holds information recorded by examination in a hospital C which is an institution, as the database S3. Each of the databases S1 to S3 indicates height, weight, blood pressure, and so on as examination item attributes, and indicates a plurality of elements belonging to these attributes.

In this case, the client terminal 101 deals with (weight, (height, blood pressure, blood, vision, LDH)) for the hospitals A to C as (matching attribute, required attribute), for example, based on operation by a client. Then, the client terminal 101 sends an analysis attribute request indicating (weight, (height, blood pressure, blood, vision, LDH)) to the institution terminals 111-113 of the hospitals A to C.

The institution terminals 111, 112, and 113 perform processing of each of the above described initial setting phase, converted data generating phase, analysis result outputting phase, and required attribute outputting phase. As a result, the institution terminal 111 encrypts (weight), (height, blood pressure, blood, vision, LDH)=(90), (159, 155, A, 0.7, 150) contained in the database S1 held by oneself, and sends them to the client terminal 101 as analysis result. The institution terminal 112 encrypts (weight), (height, blood pressure, blood, vision, LDH)=(90), (155, 160, O, 0.7, 227) contained in the database S2 held by oneself, and sends them to the client terminal 101 as analysis result. The institution terminal 113 encrypts (weight), (height, blood pressure, blood, vision, LDH)=(90), (160, 163, AB, 1.0, 264) contained in the database S3 held by oneself, and sends them to the client terminal 101 as analysis result.

The client terminal 101 acquires the analysis results sent from the institution terminals 111, 112, and 113. Accordingly, from each of the databases S1, S2, and S3, the client terminal 101 acquires, as output elements, elements of height, blood pressure, blood, vision, and LDH which belongs to a common element associated with "90" of weight in the respective databases S1, S2, and S3. Thereby, the client terminal 101 can acquire numerical values and the like of height, blood pressure, blood, vision, and LDH of persons having weight "90" who examined at each of the hospitals A to C. As a result, more data can be collected since data is collected from a plurality of institutions (hospitals in the above described example). In other words, since matching results of data from a plurality of institutions can be integrated, more data can be collected, and better analysis result can be obtained. For example, an analysis result indicating that obese patients have high blood pressure can be obtained.

As described above, in the data analysis system 100 of the present embodiment, a client operating the client terminal 101 can integrate medical examination records of patients having weight "90" while keeping medical examination data of the hospitals A to C secret from each other. Therefore, integrated analysis of medical examination records from the hospitals is possible, and medical examination records of patients having weight "90" can be shared among the hospitals without revealing any privacy data. Further, any medical examination records of patients other than having weight "90" can be kept secret.

Figure 8:
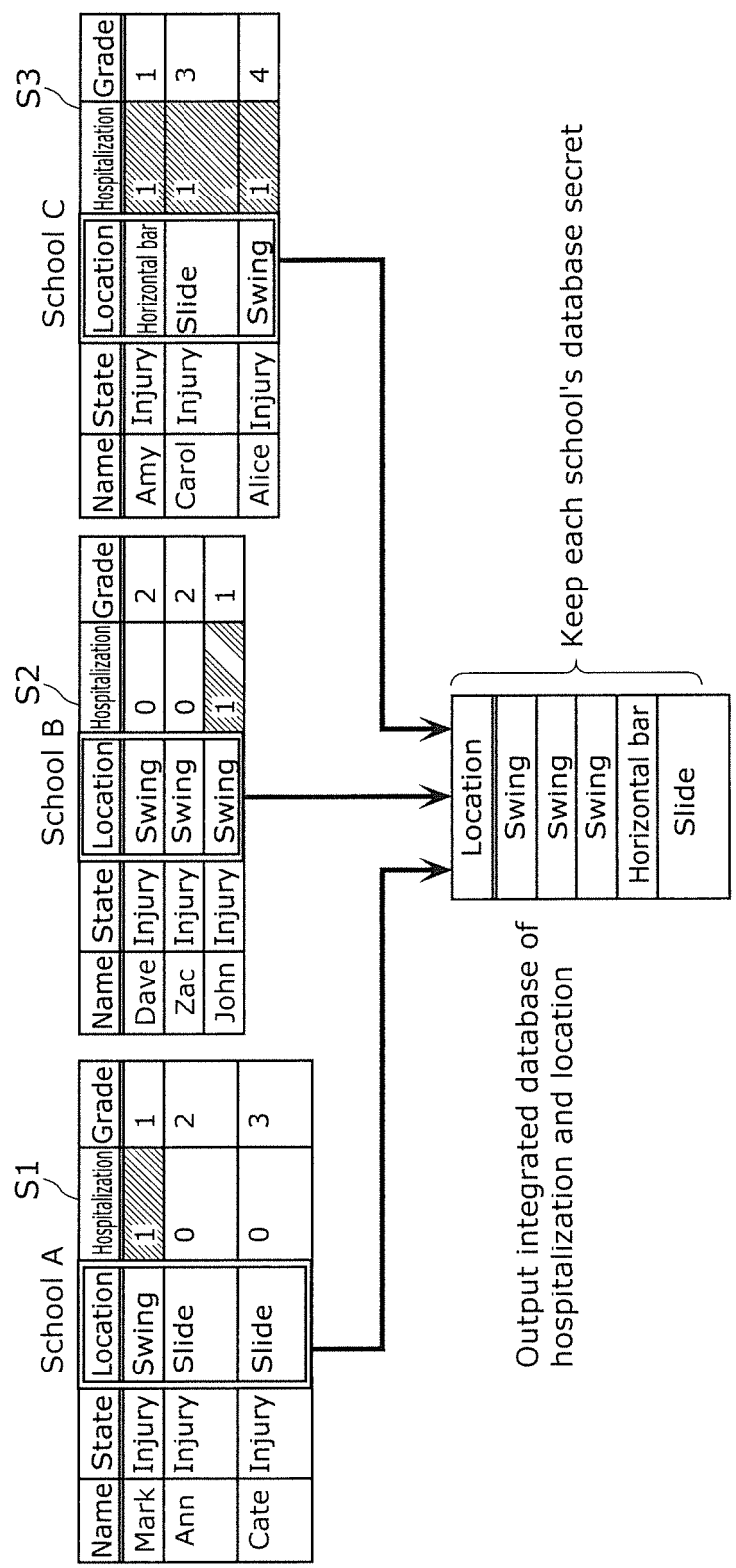
FIG. 8 is a diagram illustrating a further example of analysis by the data analysis system of the embodiment.

FIG. 8 is a diagram illustrating a further example of analysis by the data analysis system 100.

For example, the institution terminal 111 holds information about accidents that occurred at a school A which is an institution, as the database S1. The institution terminal 112 holds information about accidents that occurred at a school B which is an institution, as the database S2. The institution terminal 113 holds information about accidents that occurred at a school C which is an institution, as the database S3. Each of the databases S1 to S3 indicates name, state, location, hospitalization (hospitalized or not), and so on as attributes of accident information, and indicates a plurality of elements belonging to these attributes.

In this case, the client terminal 101 deals with (hospitalization, location) for the schools A to C as (matching attribute, required attribute), for example, based on operation by a client. Then, the client terminal 101 sends an analysis attribute request indicating (hospitalization, location) to the institution terminals 111-113 of the schools A to C.

The institution terminals 111, 112, and 113 perform processing of each of the above described initial setting phase, converted data generating phase, analysis result outputting phase, and required attribute outputting phase. As a result, the institution terminal 111 encrypts ((hospitalization), (location))=((1), (swing)) contained in the database S1 held by oneself, and sends them to the client terminal 101 as analysis result. The institution terminal 112 encrypts ((hospitalization), (location))=((1), (swing)) contained in the database S2 held by oneself, and sends them to the client terminal 101 as analysis result. The institution terminal 113 encrypts ((hospitalization), (location))=((1), (swing)), ((1), (horizontal bar)), ((1), (slide)) contained in the database S3 held by oneself, and sends them to the client terminal 101 as analysis result.

The client terminal 101 acquires the analysis results sent from the institution terminals 111, 112, and 113. Accordingly, from each of the databases S1, S2, and S3, the client terminal 101 acquires, as output elements, elements of location which belongs to a common element associated with "1" of hospitalization in the respective databases S1, S2, and S3. As a result, more data can be collected since data is collected from a plurality of institutions (schools in the above described example). In other words, since data from a plurality of institutions can be integrated, more data can be collected, and better analysis result can be obtained. In the case of the above described example, the client terminal 101 can recognize a location where an accident leading to hospitalization occurred. For example, it can be recognized that there are many accidents leading to hospitalization at swings.

As described above, in the data analysis system 100 of the present embodiment, data of the schools A to C is collected while keeping privacy about the institutions as the schools A to C and individuals, so that identification of accident causes can be improved.

Figure 9:
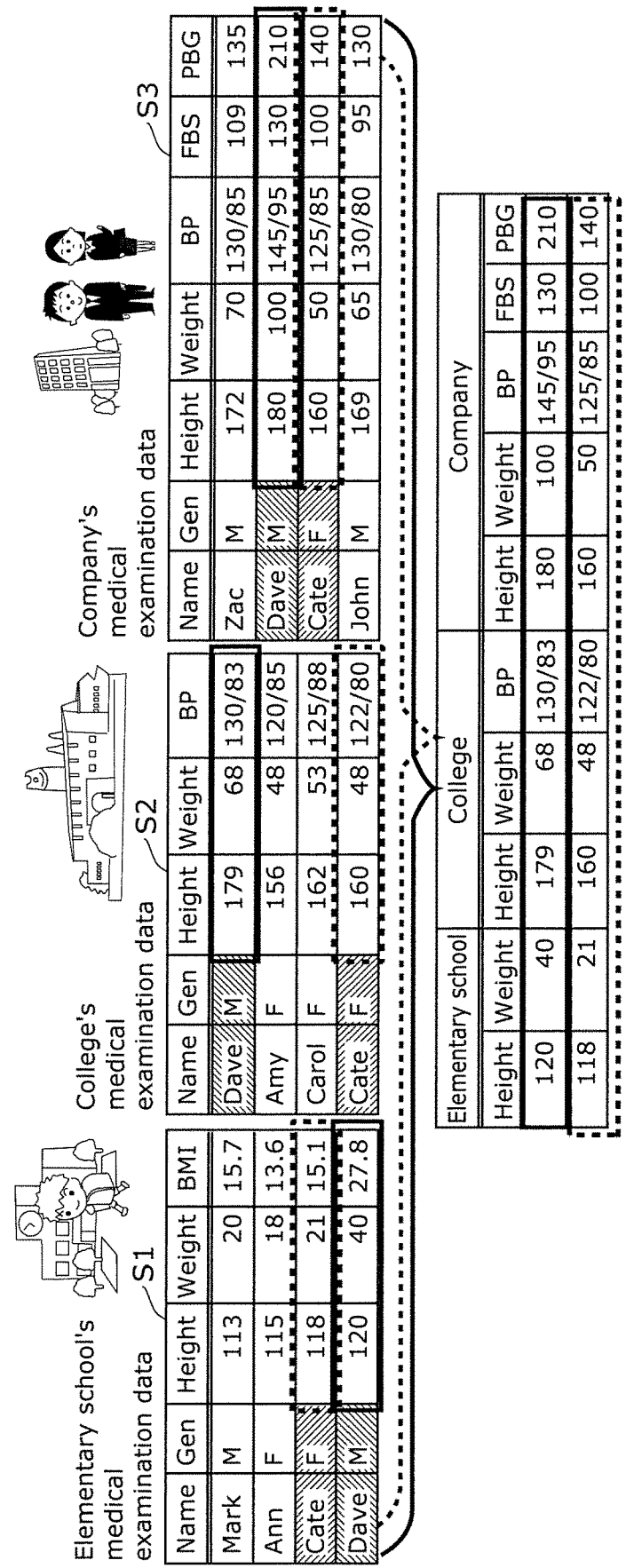
FIG. 9 is a diagram illustrating a further example of analysis by the data analysis system of the embodiment.

FIG. 9 is a diagram illustrating a further example of analysis by the data analysis system 100.

For example, the institution terminal 111 holds information recorded by medical examination at an elementary school which is an institution, as the database S1. The institution terminal 112 holds information recorded by medical examination at a college which is an institution, as the database S2. The institution terminal 113 holds information recorded by medical examination at a company which is an institution, as the database S3. Each of the databases S1 to S3 indicates name, gender, height, weight and so on as medical examination item attributes. In addition, the database S1 further indicates BMI as an examination item attribute, the database S2 further indicates BP (blood pressure) as an examination item attribute, and the database S3 further indicates BP, FBS (fasting blood glucose), and PBG (postprandial blood glucose) as examination item attributes. In addition, databases S1 to S3 indicate a plurality of elements belonging to these attributes.

In this case, the client terminal 101 deals with ((name, gender), (height, weight)) for the elementary school as (matching attribute, required attribute), for example, based on operation by a client. Then, the client terminal 101 sends an analysis attribute request indicating the ((name, gender), (height, weight)) to the institution terminal 111 of the elementary school. Further, the client terminal 101 deals with ((name, gender), (height, weight, BP)) for the college as (matching attribute, required attribute), for example, based on operation by the client. Then, the client terminal 101 sends an analysis attribute request indicating the ((name, gender), (height, weight, BP)) to the institution terminal 112 of the college. Further, the client terminal 101 deals with ((name, gender), (height, weight, BP, FBS, PBG)) for the company as (matching attribute, required attribute), for example, based on operation by the client. Then, the client terminal 101 sends an analysis attribute request indicating the ((name, gender), (height, weight, BP, FBS, PBG)) to the institution terminal 113 of the company.

The institution terminals 111, 112, and 113 perform processing of each of the above described initial setting phase, converted data generating phase, analysis result outputting phase, and required attribute outputting phase. As a result, the institution terminal 111 of the elementary school encrypts (height, weight)=(120, 40) to E(120, 40) associated with (name, gender)=(Dave, M), and encrypts (118, 21) to E(118, 21) associated with (name, gender)=(Cate, F) contained in the database S1 held by oneself, and sends (E(120, 40), E(118, 21)) to the client terminal 101 as analysis result.

The institution terminal 112 of the college encrypts (height, weight, BP)=(179, 68, 130/83) to E(179, 68, 130/83) associated with (name, gender)=(Dave, M), and encrypts (160, 48, 122/80) to E(160, 48, 122/80) associated with (name, gender)=(Cate, F) contained in the database S2 held by oneself, and sends (E(179, 68, 130/83), E(160, 48, 122/80)) to the client terminal 101 as analysis result.

The institution terminal 113 of the company encrypts (height, weight, BP, FBS, PBG)=(180, 100, 145/95, 130, 210) to E(180, 100, 145/95, 130, 210) associated with (name, gender)=(Dave, M), and encrypts (160, 50, 125/85, 100, 140) to E(160, 50, 125/85, 100, 140) associated with (name, gender)=(Cate, F) contained in the database S3 held by oneself, and sends (E(180, 100, 145/95, 130, 210), E(160, 50, 125/85, 100, 140)) to the client terminal 101 as analysis result.

The client terminal 101 acquires the analysis results sent from the institution terminals 111, 112, and 113. Accordingly, from the databases S1, S2, and S3, the client terminal 101 acquires, as output elements, elements of height, weight, BP, FBS, and PBG associated with "Dave, M" which is a common element belonging to name and gender in the respective databases S1, S2, and S3. Further, from the databases S1, S2, and S3, the client terminal 101 acquires, as output elements, elements of height, weight, BP, FBS, and PBG associated with "Cate, G" which is a common element belonging to name and gender in the respective databases S1, S2, and S3. As a result, the client terminal 101 can acquire numerical values of height and weight of the same person who had medical examination at the elementary school, the college, and the company. Therefore, the client terminal 101 can acquire analysis results through the person's growth process.

As described above, in the data analysis system 100 of the present embodiment, while data of each institution, that is, the elementary school, college, and company is kept secret, time-series data about the same person across those institutions can be integrated.

Conclusion

As described above, according to a data analysis method of the data analysis system 100 in the present embodiment, in the analysis attribute inputting phase, the client terminal 101 requests the institution terminals 111-114 to perform analysis of a matching attribute, wherein the institution terminals 111-114 hold the respective databases S1 to S4, each of which indicates a plurality of elements with respect to each of one or more attributes. Next, in the converted data generating phase, in response to the request from the client terminal 101, each of the institution terminals 111-114 performs conversion processing including encryption on an element belonging to the matching attribute within the database of the institution terminal, and sends converted data obtained by the conversion processing to the outsource terminal 102. Then, in the converted data integrating phase, the outsource terminal 102 integrates a plurality of the converted data sent from the institution terminals 111-114 to generate integrated converted data, and sends the integrated converted data to each of the institution terminals 111-114. Then, in the analysis result outputting phase, each of the institution terminals 111-114 compares each of the plurality of elements belonging to the matching attribute within the database of the institution terminal with the integrated converted data sent from the outsource terminal 102, thereby identifying, as a common element, an element belonging to the matching attribute and held in common by the institution terminals 111-114.

In this way, the outsource terminal 102 integrates converted data sent from each of the institution terminals 111-114, and the integrated converted data composed of the integrated plurality of converted data is sent to each of the institution terminals 111-114. Therefore, the institution terminals 111-114 bear not all of the computation required for analysis of the matching attribute, that is, comparison of the matching attribute, and a part of the computation for the institution terminals 111-114 can be aggregated on the outsource terminal 102. As a result, even if the number of institution terminals subjected to analysis, that is, the number of institutions increases, the overall amount of computation required for data analysis can be restrained, and the time required for data analysis can be shortened. In other words, while conventionally, the load of data analysis depends on the number of institutions, such dependency can be restrained. In addition, data can be restrained from being collected by one institution, and it is possible to request the outsource terminal 102 to perform computation which depends on the number of institutions.

In addition, since converted data sent from each of the institution terminals 111-114 to the outsource terminal 102 has been encrypted, the outsource terminal 102 cannot decrypt the converted data to the elements even if acquiring the converted data. However, even though the converted data cannot be decrypted, the integrated converted data necessary for identifying a common element is generated by the outsource terminal 102. Therefore, according to a data analysis method of the present invention, the outsource terminal 102 does not need to be a terminal device of a reliable institution which keeps data secret, and the practicality can be improved.

In addition, the integrated converted data sent from the outsource terminal 102 to each of the institution terminals 111-114 is data into which a plurality of converted data are integrated. Therefore, even if each of the institution terminals 111-114 acquires the integrated converted data from the outsource terminal 102 and further decrypts it, each of the institution terminals cannot know elements held by the other institution terminals except for the common element. Accordingly, the content of the database S1 to S4 held by each of the institution terminals 111-114 can be kept secret from the other institution terminals as well as the outsource terminal 102. As a result, for example, privacy can be protected.

In addition, in the present embodiment, when performing the conversion processing on the element belonging to the matching attribute, each of the institution terminals 111-114 applies a Bloom filter to the element to convert the element to a BF value including at least one integer, and encrypts the BF value.

Accordingly, since the elements are converted to BF values independent from their data size, the load of comparing each of the plurality of elements belonging to the matching attribute within the database with the integrated converted data can be reduced, so that processing speed can be improved.

In addition, the present embodiment, the client terminal 101 further requests each of the institution terminals 111-114 to perform analysis of a required attribute. Each of the institution terminals 111-114 further selects, as an output element, an element associated with the common element from a plurality of elements belonging to the required attribute indicated by the database held by the institution terminal, and sends, as an analysis result, the common element and the output element to the client terminal 101.

In conventional data analysis methods, data stored in each institution is treated as a set of a plurality of elements belonging to one attribute. However, data has a plurality of attributes in general, and the conventional data analysis methods cannot handle such data having a plurality of attributes, and are not stable for practical use. On the other hand, in the present embodiment, not only a matching attribute but also a required attribute are analyzed as described above. Thereby, typical data having a plurality of attributes (i.e., database) can be handled, and the practicality can be further improved.

By the way, in the present embodiment, a request for analysis of a required attribute is made together with a request for analysis of a matching attribute, as an analysis attribute request. However, a request for analysis of a required attribute may be made after a request for analysis of a matching attribute.

Additionally, in the present embodiment, the client terminal 101 further acquires the analysis results sent respectively from the institution terminals 111-114, and integrates the output elements contained respectively in the plurality of analysis results.

Thereby, the common and output elements sent from each of the institution terminals 111-114 are acquired by the client terminal 101, and the common elements and the output elements from the institution terminals 111-114 are integrated by the client terminal 101. Thereby, integration of any databases can be securely realized while privacy is protected, dependency on the number of institutions is prevented, and the number of attributes of the databases is not restricted.

OTHER MODIFIED EXAMPLES

Although the client terminal 101 is a terminal device independent from the institution terminals 111-114 in the above described embodiment, the client terminal 101 may be one of the institution terminals 111-114. In this case, the institution terminal as the client terminal 101 requests a plurality of remaining institution terminals to perform analysis of the matching attribute, wherein the remaining institution terminals are the institution terminals 111-114 excluding the client terminal 101.

Further, in the above described embodiment, the outsource terminal 102 may be one of the institution terminals 111-114. In this case, the institution terminal as the outsource terminal 102 sends the integrated converted data to a plurality of remaining institution terminals, in which the remaining institution terminals are the institution terminals 111-114 excluding the outsource terminal 102.

By the way, in the above described embodiment, each of n institution terminals which receives an analysis attribute request identifies a common element held in common by all of the n institution terminals. However, each of the n institution terminals which receives an analysis attribute request may identify a common element held in common by only d ($2 \leq d \leq n-1$) institution terminals In this case, in the converted data generating phase of FIG. 3, each of the n institution terminals generates converted data by encrypting BF(Si) without calculating BF(Si)−1=[BFi[0]−1, . . . , BFi[m−1]−1] from BF(Si)=[BFi(0), BFi(m−1)]. Further, in the converted data integrating phase of FIG. 3, the outsource terminal 102 generates integrated converted data without randomizing encrypted data. Then, in the analysis result outputting phase of FIG. 3, each of the n institution terminals matches BF(Si) of each value of the matching attribute of each element of the set S1 with IBU(∪Si)=[(ΣBFi[0]), . . . , (ΣBFi[m−1])], thereby finding out a common element which is an element common in d institution terminals, from the set S1 of the matching attribute. For example, if BF(Si) of an element associated with the matching attribute common in d institution terminals is an array (1, 0, 1, 1, . . . 0, 1), MU (∪Si) will be an array (d, a, d, d, . . . b, d) (where a and b are arbitrary values) in the same way as the above. Therefore, the institution terminal i finds out, as a common element, an element of BF(Si) in which an element of 1 is placed in the same position as an element having a value d of IBU(∪Si), from among BF(Si) of a plurality of elements contained in the set S1 held by oneself.

Embodiment 2

In this embodiment, a PDDI (Privacy-preserving Distributed Data Integration) system using the data analysis system of the above described embodiment 1 will be described.

Figure 10:
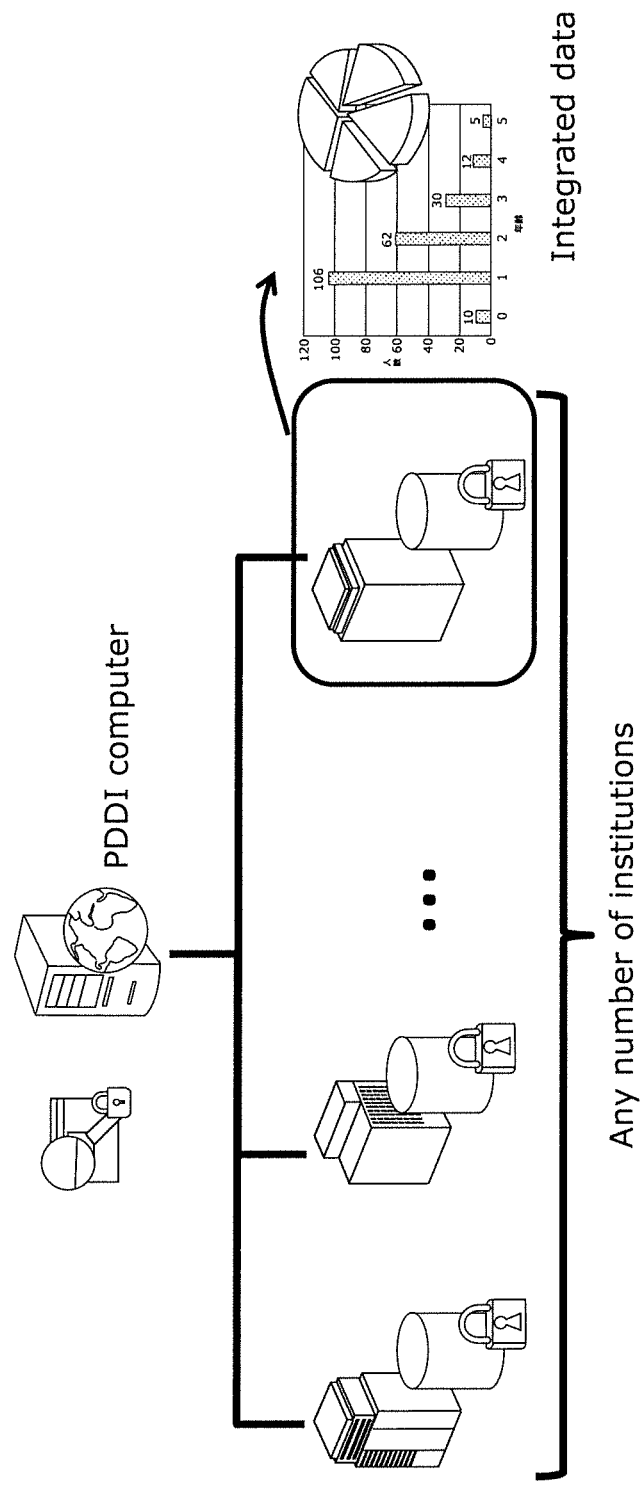
FIG. 10 is a diagram for illustrating a PDDI.

FIG. 10 is a diagram for illustrating a PDDI.

The PDDI system achieves integration of data owned by a plurality of institutions without concerning about information leakage. The following (1) to (3) can be achieved by PDDI. (1) Conversion of small data to big data with privacy protection. (2) High accuracy analysis with privacy protection by integration of rare data of institutions. (3) Diversified analysis with privacy protection by integration of different attributes of institutions.

In addition, the PDDI system has the following features (1) to (4). (1) High confidentiality: Only data permitted by each of institutions can be viewed by only an authorized institution. (2) High versatility: There is no dependency on the number of data and the number of institutions. Target institutions, matching items, and output items can be freely set. (3) Easy Introduction: No data depository facility is required. (4) High speed: PDDI computer improves processing speed while keeping data secrecy.

Figure 11:
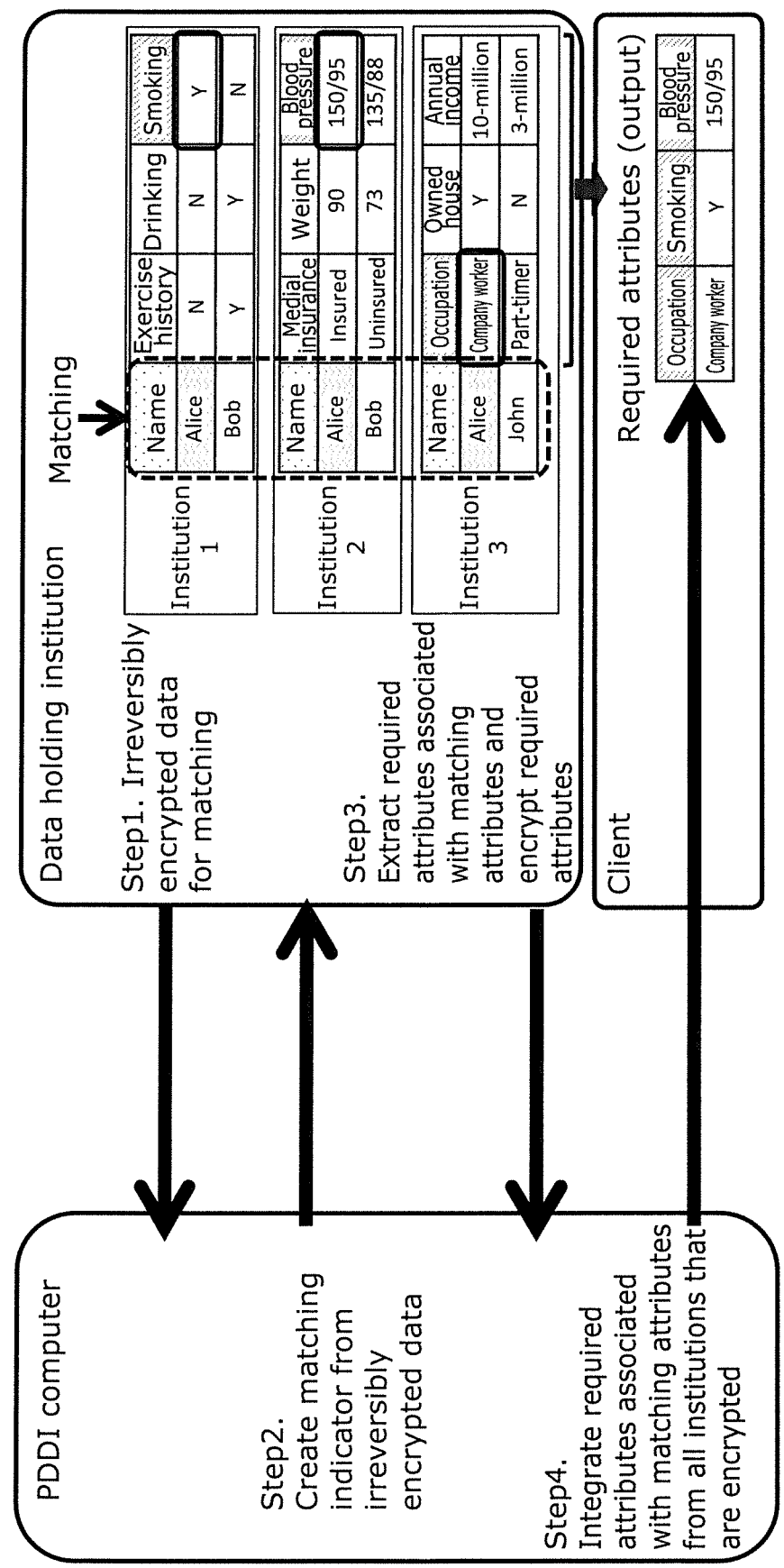
FIG. 11 is a diagram for illustrating a system model.

FIG. 11 is a diagram for illustrating a system model.

A data holding institution provides data and sets use permission attribute. A PDDI computer covers computation processing which depends on the number of institutions. In addition, the PDDI computer cannot know about data. A client (terminal) obtains a matched required attribute. Additionally, the client may act also as the data holding institution. Further, information is dispersion-managed, and is not sent from each institution to the other institutions. In this context, a matching attribute is an attribute used as a matching indicator, and a required attribute is an attribute sent to a client after matching.

Figure 12:
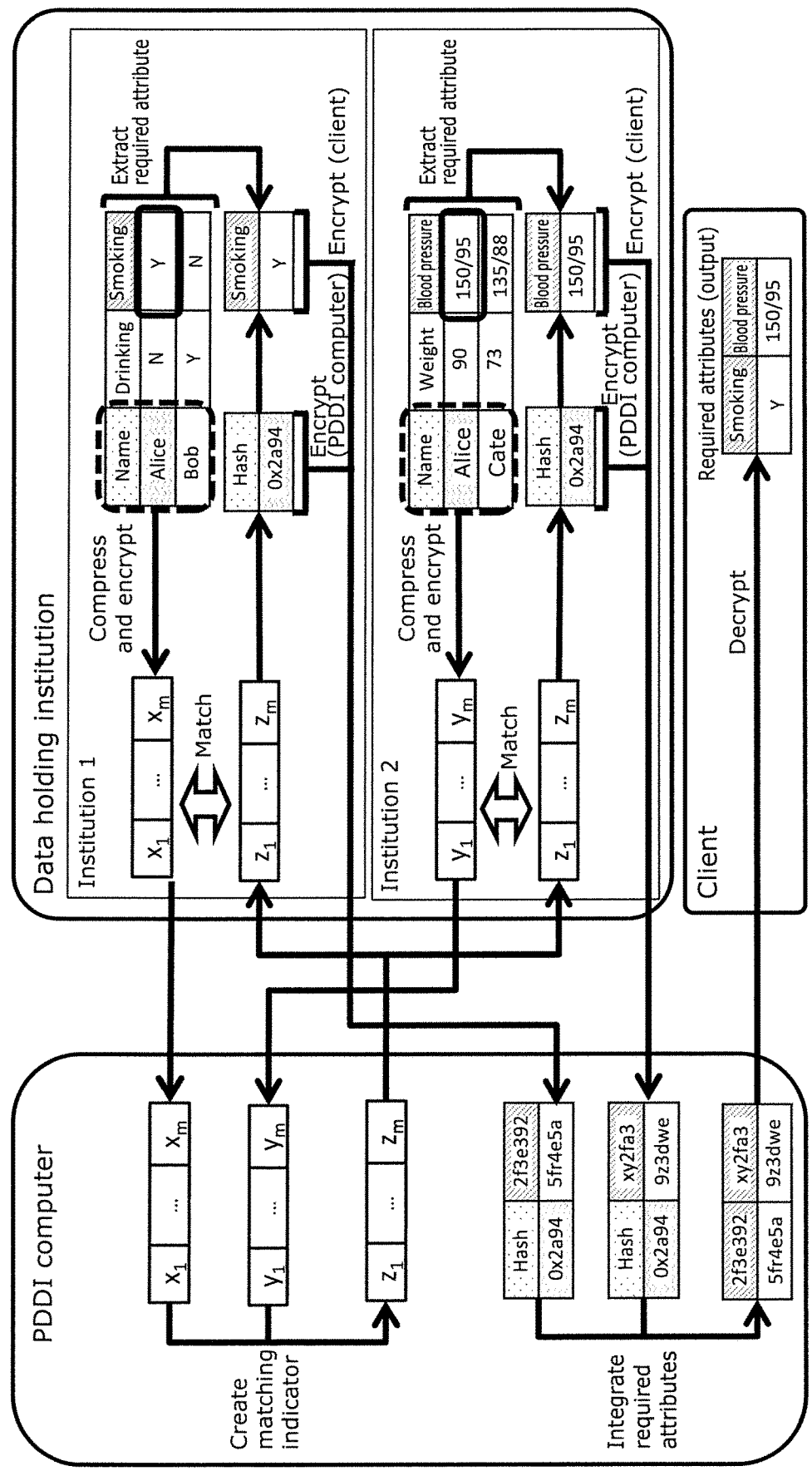
FIG. 12 is a diagram illustrating system operation and features.

FIG. 12 is a diagram illustrating system operation and features.

Since irreversibly encrypted data is passed to the PDDI computer, matching data held by the data holding institution is kept completely secret without being output to the outside of the institution. The client obtains only an attribute permitted by each institution, and does not obtain the other information. Institutions except authorized one cannot decode it since all the communication paths are encrypted.

Figure 13:
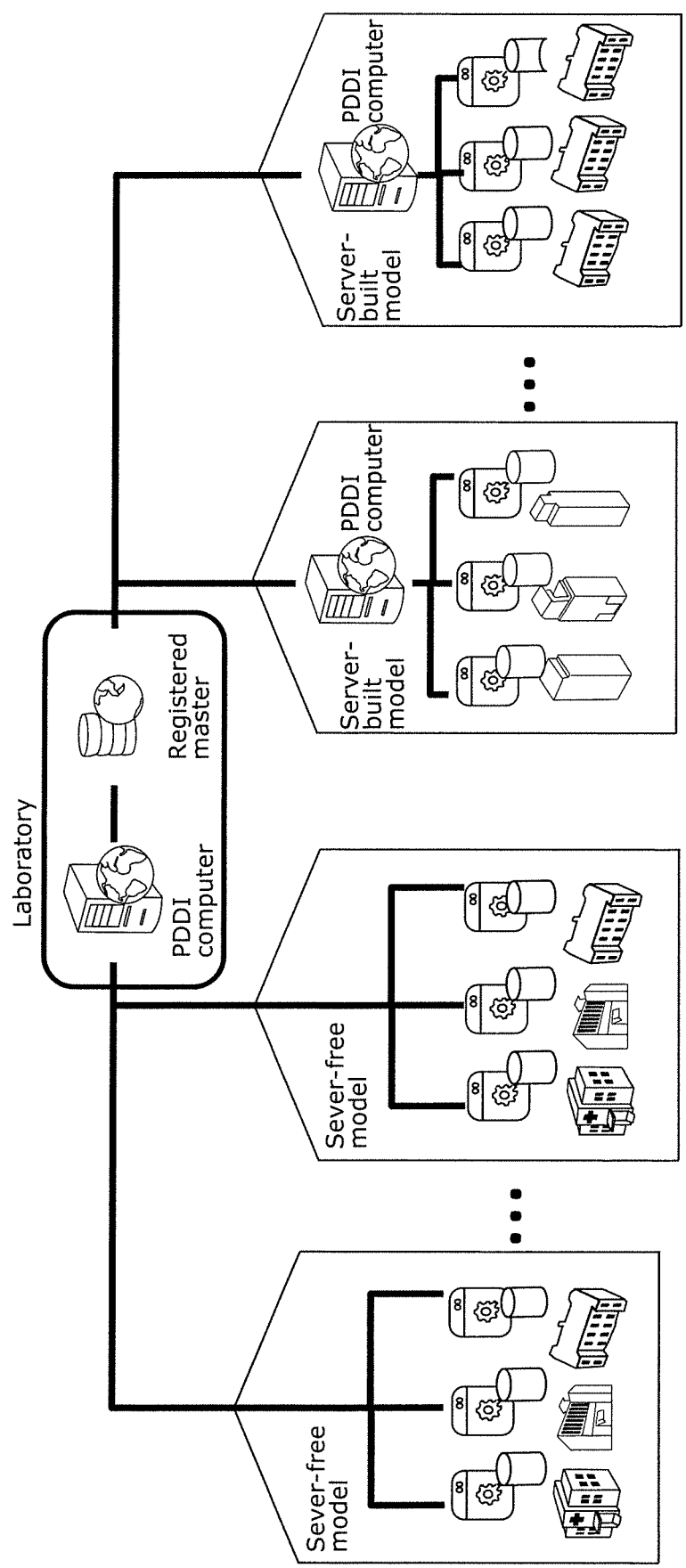
FIG. 13 is a diagram illustrating an outline of introduction of a PDDI system.

FIG. 13 is a diagram illustrating an outline of introduction of a PDDI system.

PDDI system performs matching using encryption of lossy-compressed data, and encrypts integrated data and sends it to a user, so that data matching is performed while each institution stores data independently. In this system, matching data does not get out of each institution. Integrated data is kept secret from the outside entirely except for a required institution.

In a computer-free model, no PDDI computer is required to be built, and a cloud of a laboratory is used. On the other hand, in a computer-built model, a PDDI computer is built for each group. In both of the models, matching data and integrated data are kept secret completely.

Figure 14:
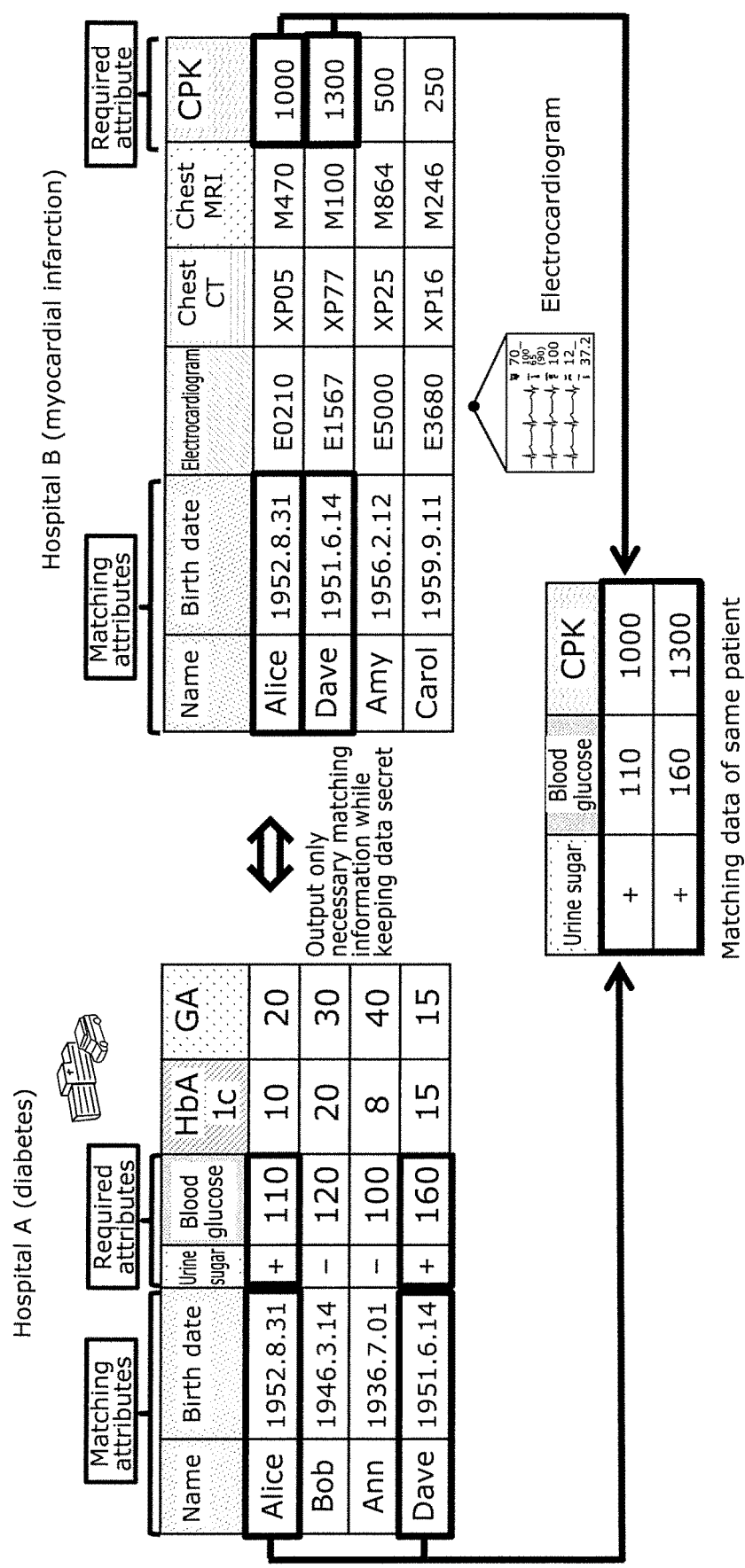
FIG. 14 is a diagram illustrating the first application example.

FIG. 14 is a diagram illustrating the first application example. The first application example is integration of medical data across institutions.

Although medical data of a patient who goes to a plurality of medical institutions is managed by each of the medical institutions independently, interaction between different diseases can be analyzed from various perspectives by matching and integrating the same patient's data. The PDDI system can match and integrate the same patient's data from medical data owned by each medical institution independently, without exposing privacy information such as a name and a birth date to the outside.

Figure 15:
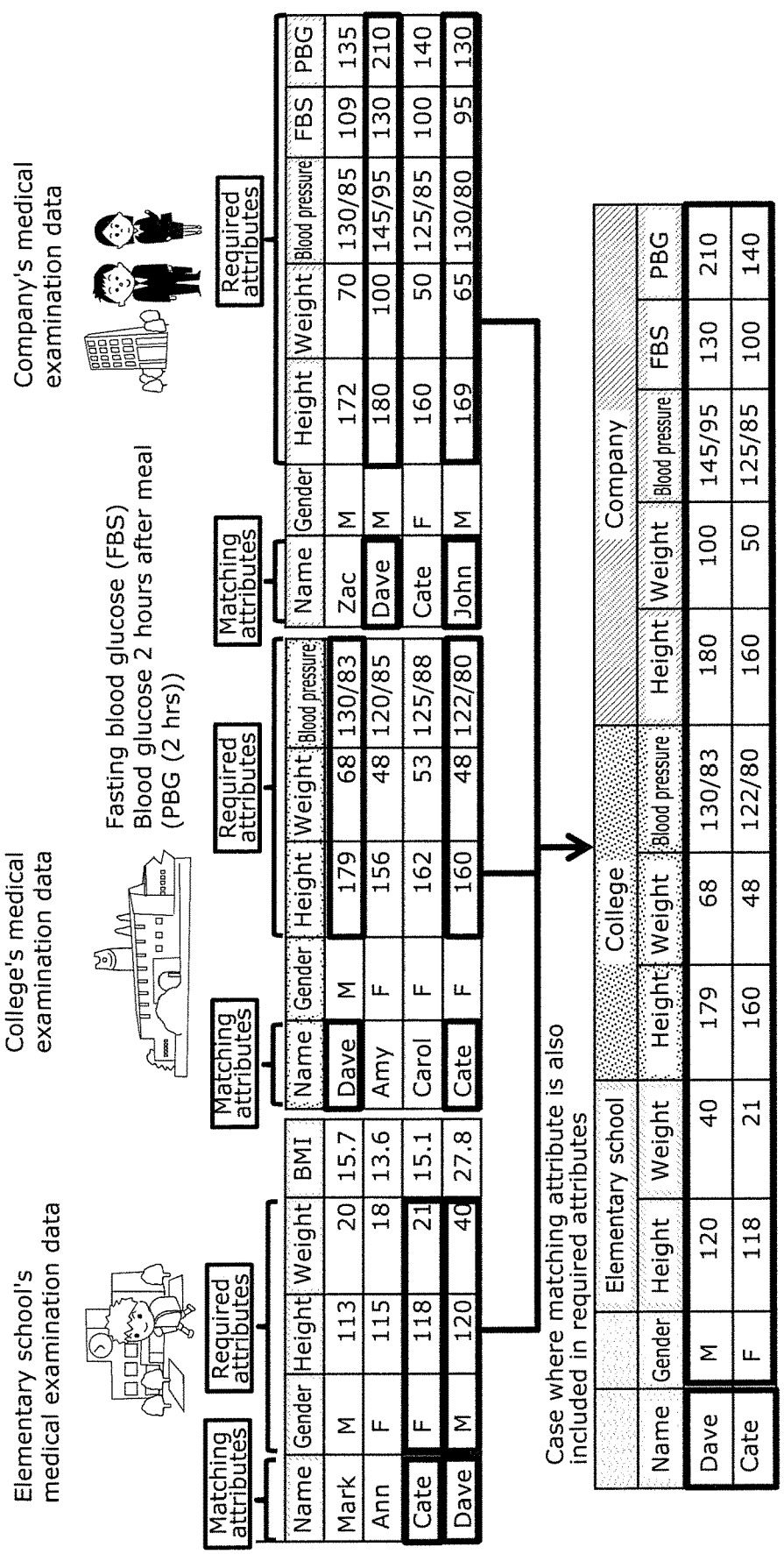
FIG. 15 is a diagram illustrating the second application example.

FIG. 15 is a diagram illustrating the second application example. The second application example is integration of medical examination data.

By integrating personal medical examination data, how an early-childhood examination value affects adulthood lifestyle diseases can be analyzed. Thereby, health guidance about lifestyle disease or the like can be effectively provided. The PDDI system can integrate the same person's medical examination data from medical examination data stored independently by a school, a company, and the like to build long-term personal medical examination data while protecting privacy. In the example shown in FIG. 15, the PDDI system performs matching of personal medical examination data as in the example of FIG. 9, and outputs the name of the person for returning the medical examination data to the person. Thereby, the medical examination data can be fed back to the person. In this case, a matching attribute is included in a required attribute. On the other hand, in a case where such personal medical examination data is used in, for example, research, the PDDI system does not use the name of the person as a required attribute.

Figure 16:
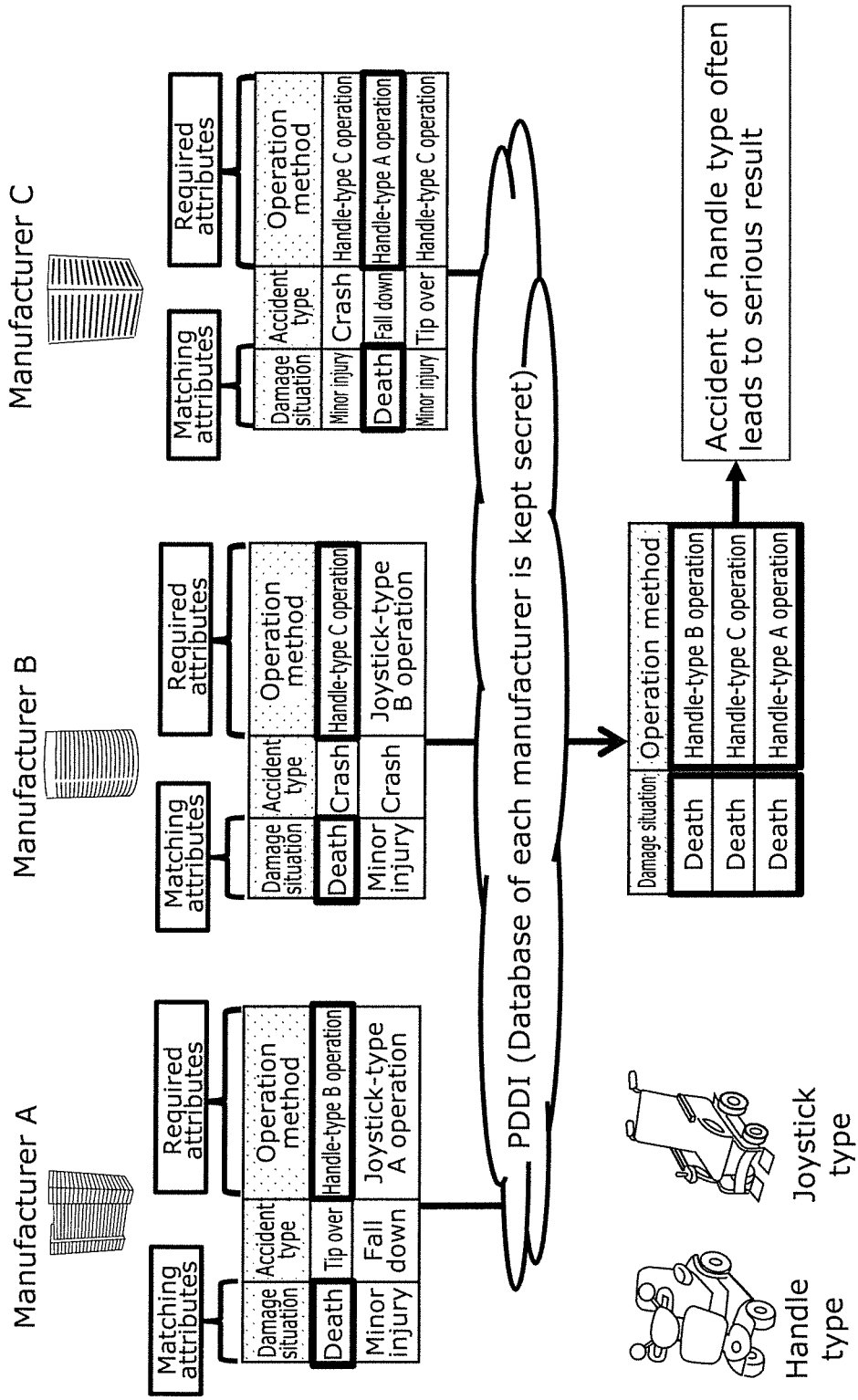
FIG. 16 is a diagram illustrating the third application example.

FIG. 16 is a diagram illustrating the third application example. The third application example is integration of accident information about electric wheelchairs.

If product accident information of each manufacturer can be integrated industry-wide, the cause of a product defect is analyzed before accident, and safe product development is facilitated. Integration of product accident information needs protection of privacy about data of each manufacturer. The PDDI system protects privacy of each manufacturer, and achieves extraction and integration of serious accident data.

Figure 17:
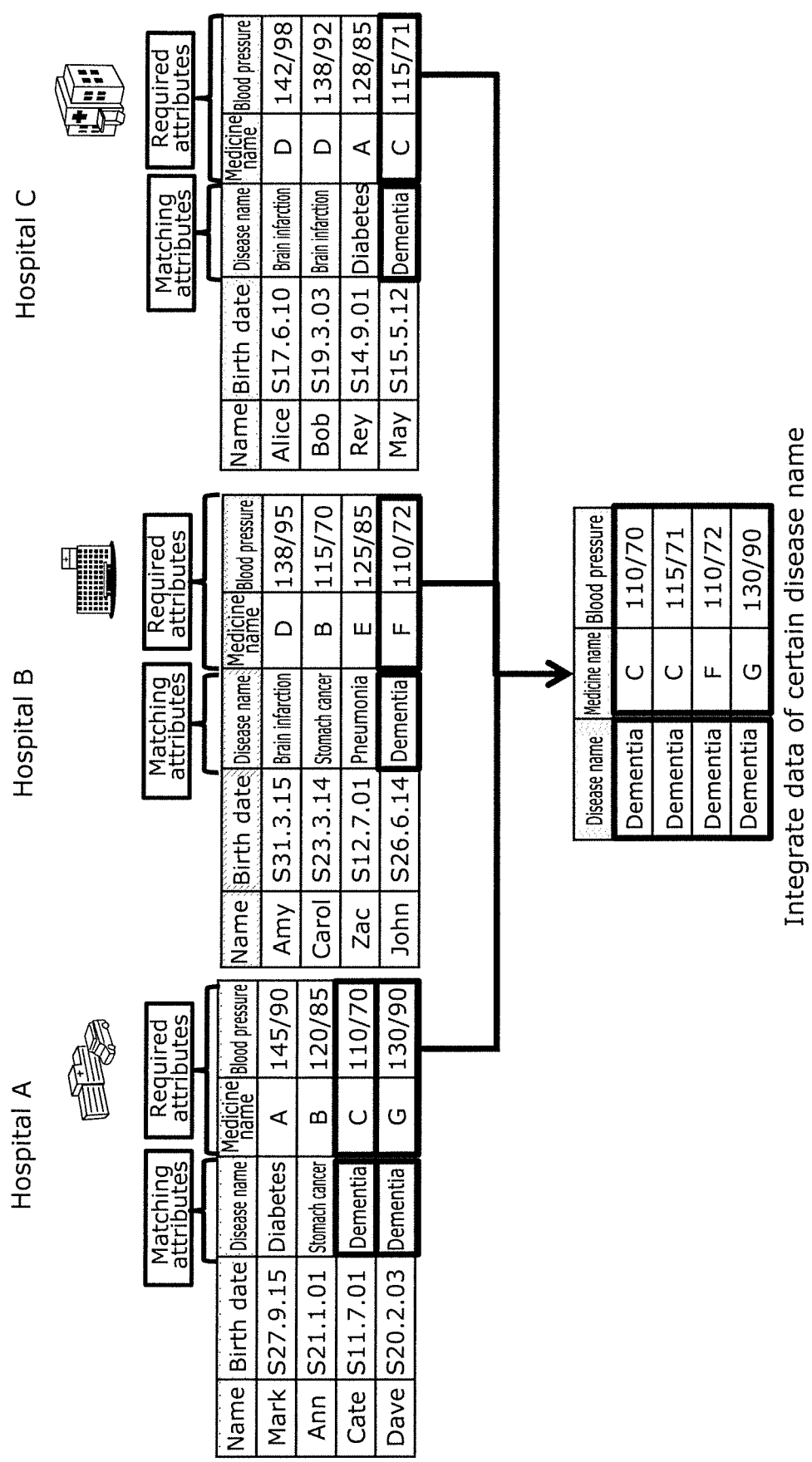
FIG. 17 is a diagram illustrating the fourth application example.

FIG. 17 is a diagram illustrating the fourth application example. The fourth application example is integration of medical treatments for the same disease.

Treatment histories with respect to a certain disease are integrated and analyzed so that effective treatments can be researched. By using the PDDI system, hospital names and personal names are kept secret.

Figure 18:
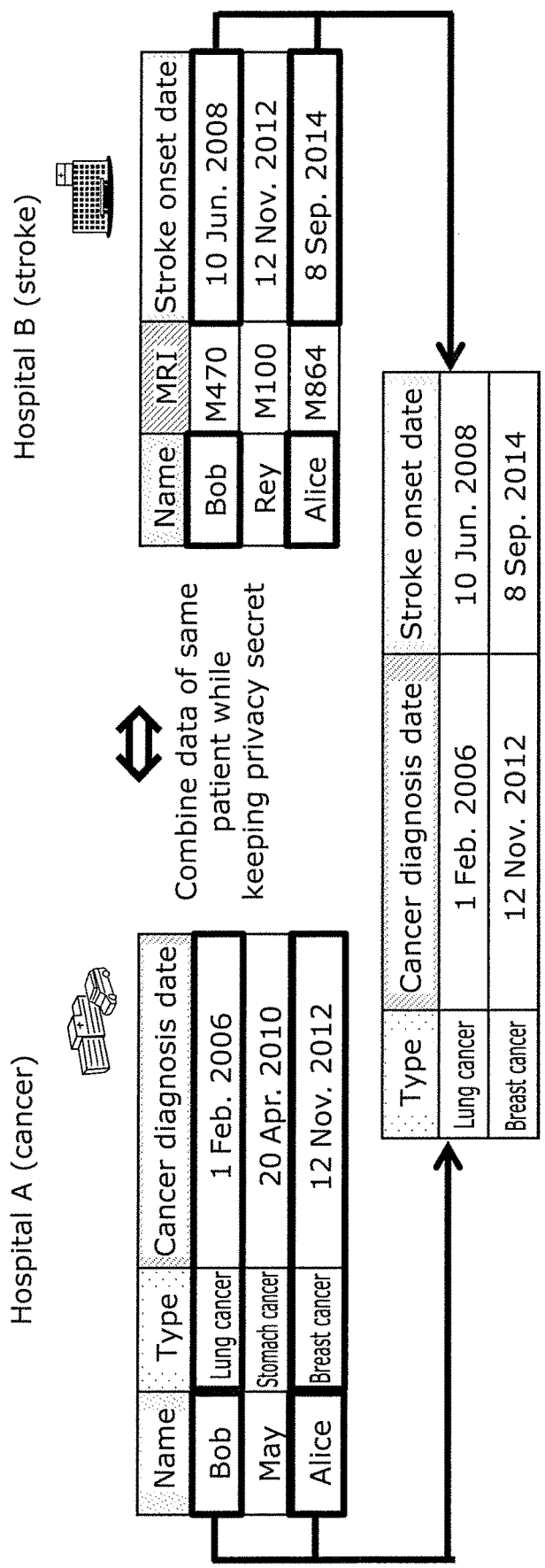
FIG. 18 is a diagram illustrating the fifth application example.

FIG. 18 is a diagram illustrating the fifth application example. The fifth application example is research on relationships between cancer and stroke.

Since many patients go to specialized hospitals for each disease, data integration is needed for researching relationships between different diseases. By using the PDDI system, data can be integrated without exposing personal information out of a hospital.

Figure 19:
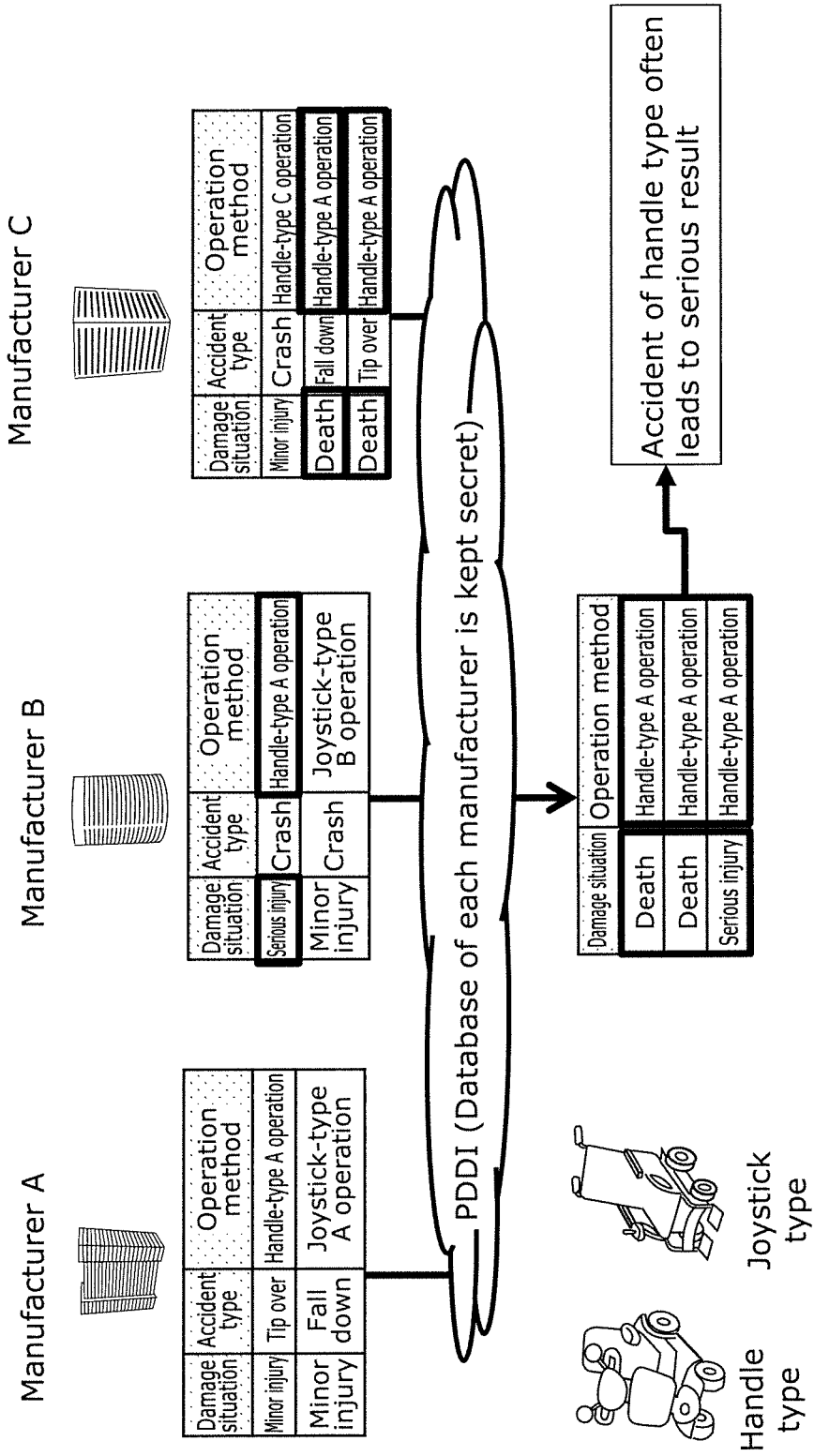
FIG. 19 is a diagram illustrating integration using a matching attribute which is performed by only a subset of institutions.

FIG. 19 is a diagram illustrating integration using a matching attribute which is performed by only a subset of institutions.

In the PDDI system as shown in FIG. 16, only "matching attributes used in all institutions" can be subjected to integration. However, as shown in FIG. 19, an attribute used in only a subset of institutions may be a matching key. In other words, in the example of FIG. 16, if there are fatal cases for all the manufacturers, the PDDI system outputs data of the fatal cases. On the other hand, in the example of FIG. 19, even if there are no fatal cases for some of the manufacturers, the PDDI system extracts and outputs data of the fatal cases. That is, extracted data is not a common set.

Figure 20:
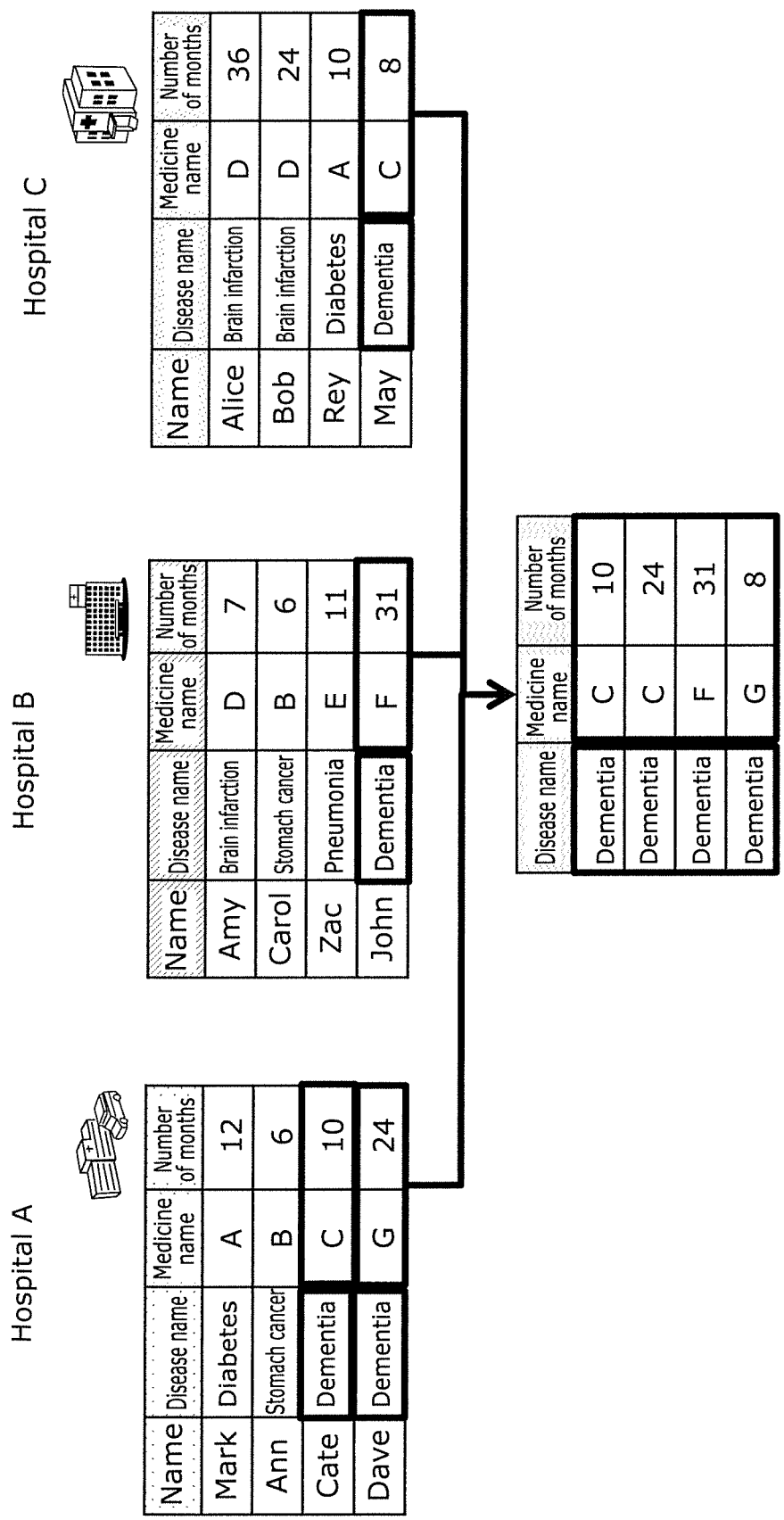
FIG. 20 is a diagram illustrating integration of data in which a matching attribute is repeated within an institution.

FIG. 20 is a diagram illustrating integration of data in which a matching attribute is repeated within an institution.

In the PDDI system, records having the same matching attribute in an institution are merged by data integration. However, even in the above case, those records may be considered as different records when subjected to integration processing. The example shown in FIG. 20 can also be considered as an example application to data extraction using a matching attribute.

Figure 21:
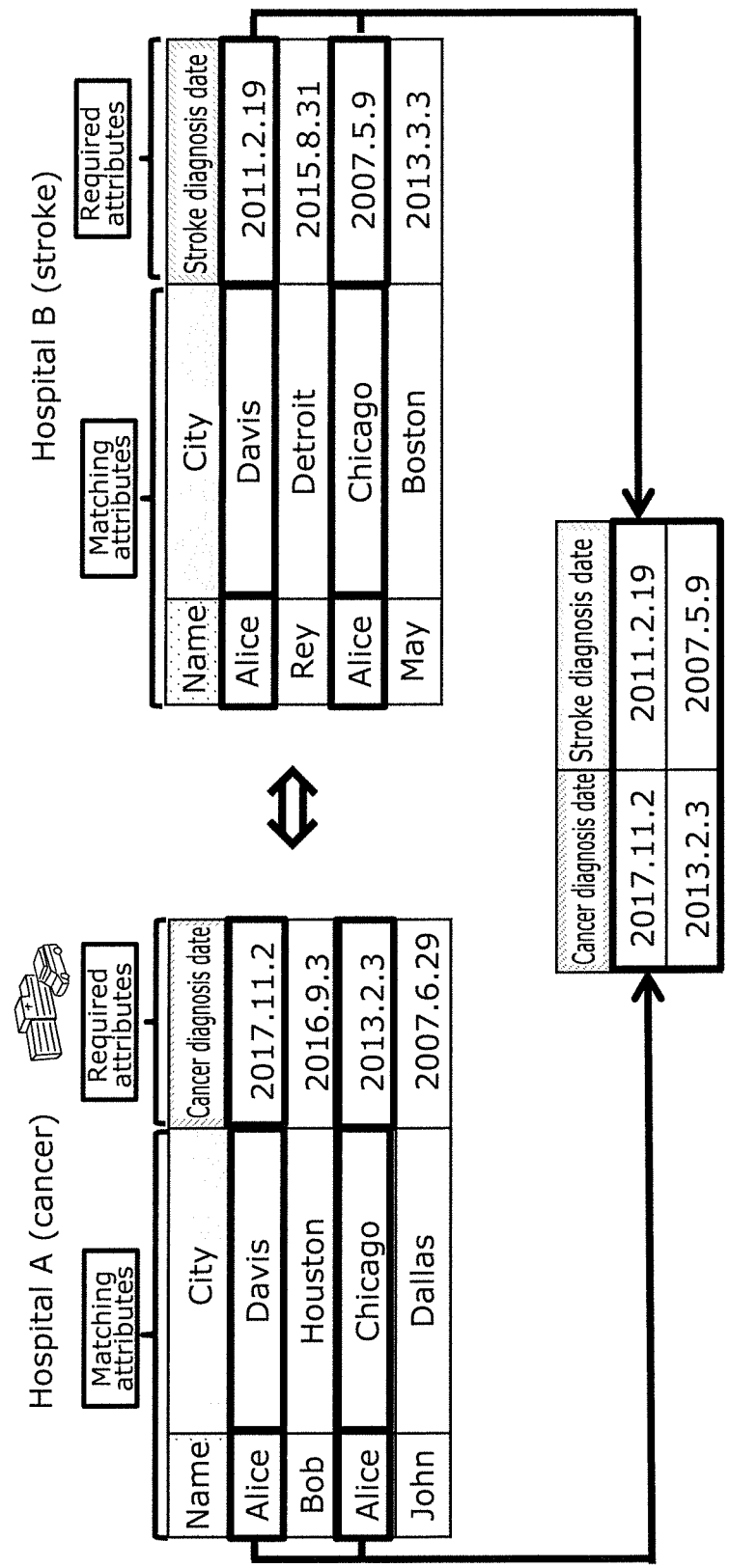
FIG. 21 is a diagram illustrating sequential extension of a matching attribute.

FIG. 21 is a diagram illustrating sequential extension of a matching attribute.

In the PDDI system, a matching attribute is fixed, and defined as AND combination of a specified attribute. However, a function may be added which extends the range of application of a matching attribute until uniqueness of matching is obtained. Specifically, if matching is impossible using only an attribute "name", the PDDI system includes an attribute "address (e.g., city)" in a matching attribute in addition to the attribute "name" as shown in FIG. 21.

Figure 22:
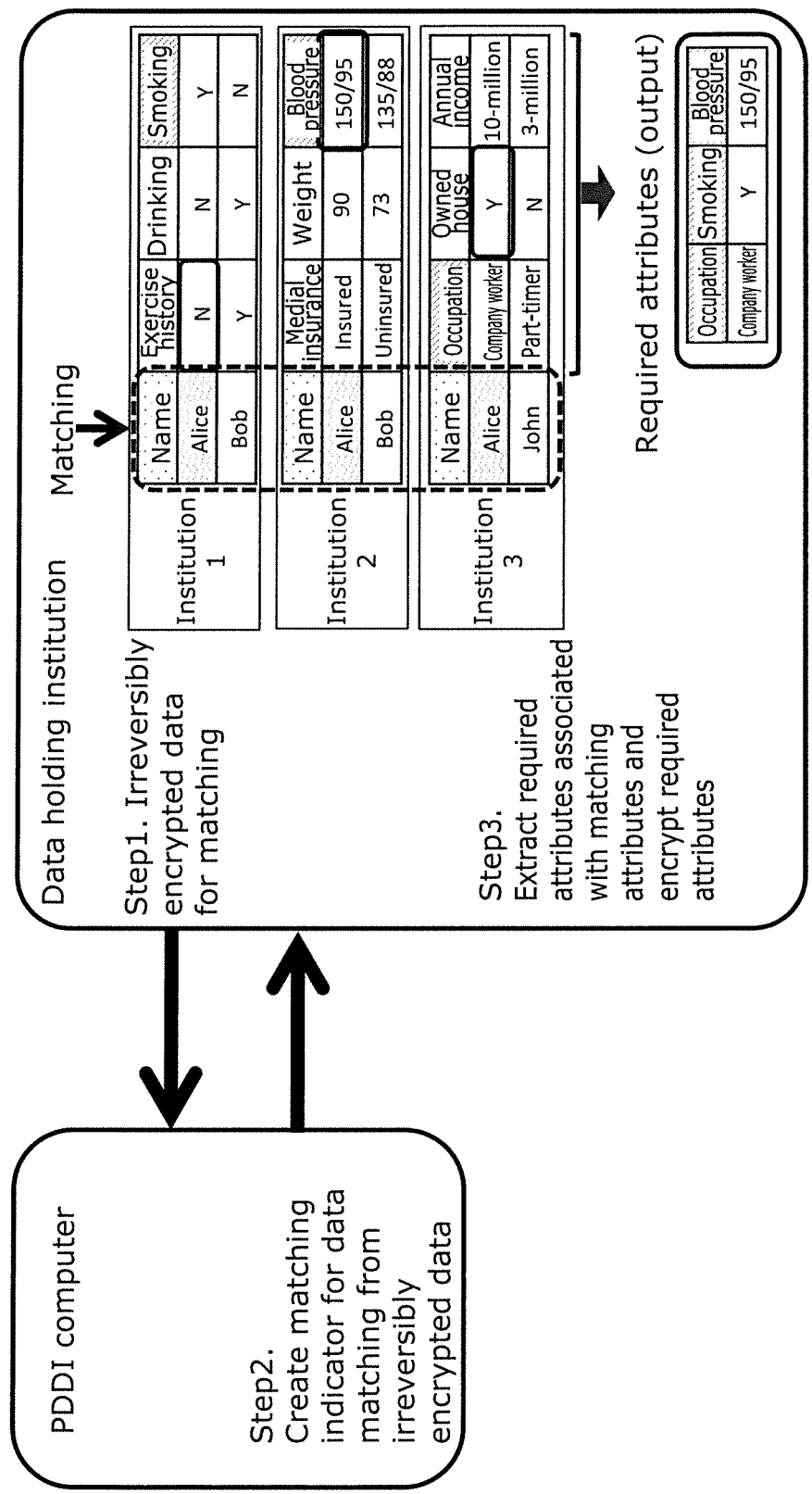
FIG. 22 is a diagram illustrating system operation and features.

FIG. 22 is a diagram illustrating system operation and features.

Since irreversibly encrypted data is passed to the PDDI computer, matching data held by the data holding institution is kept completely secret without being output to the outside of the institution. Further, only data having an attribution permitted by an institution to be exposed to a client is integrated, and therefore data more than necessary does not get out of the institution. Since all the data is encrypted before being sent and received, no one other than institutions using PDDI can intercept the communication.

In the above described each embodiment, each component may be constructed by dedicated hardware, or may be implemented by executing a software program suitable for each component. Each component may be implemented by a program execution unit such as a CPU or a processor loading and executing a software program recorded on a recording medium such as a hard disk or a semiconductor memory. It is noted that software for implementing terminals and the like of the above described embodiments is a program that causes a computer to execute the steps of the flowchart shown in FIG. 3.

In addition, "integration" in the above described embodiments means that a plurality of data are associated properly. For example, in a case where an institution A's database has (John, cancer data A) and an institution B's database has (John, myocardial infarction data X), associating (cancer data A) and (myocardial infarction data X) is called "integration". Such data association is performed using a common element associated with a matching attribute. For example, in the above described example, data association is performed using the common element "John" belonging to the matching attribute "name".

Further, a data analysis method of the present invention is a method which classifies database's attributes into a matching attribute, a required attribute, and the other attributes, and achieves protection of not only privacy of a data owner but also privacy of an institution which manages the data. Specifically, a data analysis method of the present invention performs matching of databases held by institutions with respect to a matching attribute, and integrates required attributes of data having the matching attribute in the institutions. For example, a system which performs data analysis according to the data analysis method of the present invention performs matching of databases of the institutions with respect to data "dementia" belonging to a matching attribute "disease name", and integrates data belonging to required attributes "age, drinking, smoking" held by the institutions with respect to the matched data. At this time, the system has concealed a person whose data is integrated and an institution from which data is integrated. Further, a condition for computing an actual output value may be imposed to a required attribute, for example, a condition that the required attribute is contained in two or more institutions may be imposed.

Although data analysis methods according to one or a plurality of aspects have been described heretofore based on the foregoing embodiments, the present invention is not limited to these embodiments. Forms obtained by performing various modifications to the embodiments which may be conceived by those skilled in the art without departing from the essence of the present invention, and forms obtained by combining elements in different embodiments may be included within the scope of the present invention.

INDUSTRIAL APPLICABILITY

A data analysis method of the present invention has effects that time required for data analysis is shortened, a reliable institution is unnecessary, and practicality is improved, and is useful for, for example, a system that analyzes databases of institutions such as hospitals, schools, and companies.

REFERENCE SIGNS LIST

100 Data analysis system
101 Client terminal
102 Outsource terminal
111-114 Institution terminal

The invention claimed is:

1. A data analysis method, comprising:
   by a client terminal, requesting a plurality of institution terminals to perform analysis of a matching attribute and an element associated with the matching attribute, each of the institution terminals holding a database that indicates a plurality of elements with respect to each of one or more attributes;
   by each of the plurality of institution terminals, in response to the request from the client terminal, performing conversion processing including encryption on an element belonging to the matching attribute within the database of the institution terminal, and sending converted data obtained by the conversion processing to an outsource terminal;
   by the outsource terminal, integrating a plurality of the converted data sent from the plurality of institution terminals to generate integrated converted data, and sending the integrated converted data to each of the plurality of institution terminals;
   by each of the plurality of institution terminals, comparing each matching attribute of a plurality of the elements within the database of the institution terminal with the integrated converted data sent from the outsource terminal, to identify, as a common element, an element associated with the matching attribute and held in common by at least two of the plurality of institution terminals, wherein
   when performing the conversion processing on the element belonging to the matching attribute, each of the plurality of institution terminals applies a Bloom filter to the element to convert the element to a BF value including at least one integer, and encrypts the BF value, and when generating the integrated converted data, the outsource terminal performs processing including arithmetic including at least multiplication of the plurality of the converted data to generate the integrated converted data.

2. The data analysis method according to claim 1, wherein the client terminal is one of the plurality of institution terminals and requests a plurality of remaining institution terminals to perform analysis of the matching attribute, the plurality of remaining institution terminals being the plurality of institution terminals excluding the client terminal.

3. The data analysis method according to claim 1, wherein the outsource terminal is one of the plurality of institution terminals and sends the integrated converted data to a plurality of remaining institution terminals, the plurality of remaining institution terminals being the plurality of institution terminals excluding the outsource terminal.

4. The data analysis method according to claim 1, wherein the client terminal further requests each of the plurality of institution terminals to perform analysis of a required attribute, and each of the plurality of institution terminals further selects, as an output element, an element associated with the common element from a plurality of elements belonging to the required attribute indicated by the database held by the institution terminal, and sends, as an analysis result, the output element that is associated with the common element to the client terminal.

5. The data analysis method according to claim 4, wherein the client terminal further acquires a plurality of the analysis results sent respectively from the plurality of institution terminals, and integrates the output elements contained respectively in the plurality of analysis results.

6. The data analysis method according to claim 4, wherein in requesting the analysis of the required attribute, the client terminal imposes a condition for obtaining the analysis result on each of the plurality of institution terminals.

7. The data analysis method according to claim 6, wherein in requesting the analysis of the required attribute, the client terminal imposes, as the condition, a condition that the required attribute is contained in at least two of the plurality of institution terminals.

8. A data analysis system, comprising:

a plurality of institution terminals each holding a database that indicates a plurality of elements with respect to each of one or more attributes;

a client terminal that requests the plurality of institution terminals to perform analysis of a matching attribute and an element associated with the matching attribute; and an outsource terminal, wherein in response to the request from the client terminal, each of the plurality of institution terminals performs conversion processing including encryption on an element belonging to the matching attribute within the database of the institution terminal, and sends converted data obtained by the conversion processing to the outsource terminal, the outsource terminal integrates a plurality of the converted data sent from the plurality of institution terminals to generate integrated converted data, and sends the integrated converted data to each of the plurality of institution terminals, each of the plurality of institution terminals compares each matching attribute of a plurality of the elements within the database of the institution terminal with the integrated converted data sent from the outsource terminal, to identify, as a common element, an element associated with the matching attribute and held in common by at least two of the plurality of institution terminals, when performing the conversion processing on the element belonging to the matching attribute, each of the plurality of institution terminals applies a Bloom filter to the element to convert the element to a BF value including at least one integer, and encrypts the BF value, and when generating the integrated converted data, the outsource terminal performs processing including arithmetic including at least multiplication of the plurality of the converted data to generate the integrated converted data.

* * * * *